US009896420B2

(12) United States Patent
Landry et al.

(10) Patent No.: US 9,896,420 B2
(45) Date of Patent: Feb. 20, 2018

(54) N-QUINOLIN-BENZENSULFONAMIDES AND RELATED COMPOUNDS FOR THE TREATMENT OF CANCER, AUTOIMMUNE DISORDERS AND INFLAMMATION

(71) Applicant: The Trustees of Columbia University in the City of New York, New York, NY (US)

(72) Inventors: Donald W. Landry, New York, NY (US); Owen O'Connor, Scarsdale, NY (US); Shi-Xian Deng, White Plains, NY (US); Matko Kalac, New York, NY (US); Kristen Alison Rinderspacher, Bronx, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 14/020,363

(22) Filed: Sep. 6, 2013

(65) Prior Publication Data
US 2014/0073668 A1  Mar. 13, 2014

Related U.S. Application Data

(63) Continuation of application No. PCT/US2012/028619, filed on Mar. 9, 2012.

(60) Provisional application No. 61/451,408, filed on Mar. 10, 2011.

(51) Int. Cl.
| *A01N 43/42* | (2006.01) |
| *A61K 31/47* | (2006.01) |
| *C07D 215/40* | (2006.01) |
| *A61K 31/4709* | (2006.01) |
| *C07D 409/12* | (2006.01) |

(52) U.S. Cl.
CPC ............ *C07D 215/40* (2013.01); *A61K 31/47* (2013.01); *A61K 31/4709* (2013.01); *C07D 409/12* (2013.01)

(58) Field of Classification Search
CPC ................................ A01N 43/42; A61K 31/47
USPC ........................................................ 514/314
See application file for complete search history.

(56) References Cited

U.S. PATENT DOCUMENTS

| 3,337,555 | A | 8/1967 | Billman et al. |
| 8,685,963 | B2 | 4/2014 | Landry et al. |
| 2005/0020586 | A1 | 1/2005 | Tepe |
| 2006/0024691 | A1 | 2/2006 | Benz |
| 2006/0041006 | A1 | 2/2006 | Ibrahim et al. |
| 2007/0207509 | A1 | 9/2007 | Frederickson et al. |
| 2007/0254894 | A1 | 11/2007 | Kane et al. |
| 2008/0231834 | A1 | 9/2008 | Gryczynski et al. |
| 2009/0163545 | A1 | 6/2009 | Goldfarb |
| 2009/0179553 | A1 | 7/2009 | Yakuschenko et al. |
| 2009/0218516 | A1 | 9/2009 | Gryczynski et al. |
| 2009/0220895 | A1 | 9/2009 | Garza et al. |

FOREIGN PATENT DOCUMENTS

| JP | 2000144125 | 5/2000 |
| KR | 20090015766 | 2/2009 |
| RU | 2310676 | 11/2007 |
| WO | WO 2001/057141 | 8/2001 |
| WO | WO 2001/092437 | 12/2001 |
| WO | WO 2002/004492 | 1/2002 |
| WO | WO 2002/095361 | 11/2002 |
| WO | WO 2004/094652 | 11/2004 |
| WO | WO 2004/108121 A1 | 12/2004 |
| WO | WO 2005/049026 | 6/2005 |
| WO | WO 2006/080581 | 3/2006 |
| WO | WO 2006/080582 | 3/2006 |
| WO | WO 2006/121219 | 11/2006 |
| WO | WO 2007/015017 | 2/2007 |
| WO | WO 2007/118276 | 10/2007 |
| WO | WO 2008/074068 A1 | 6/2008 |
| WO | WO 2008/131192 | 10/2008 |
| WO | WO 2008/144011 | 11/2008 |
| WO | WO 2009/056849 | 5/2009 |
| WO | WO 2009/134973 A1 | 11/2009 |
| WO | WO 2009/155088 | 12/2009 |

(Continued)

OTHER PUBLICATIONS

Lopez-Rodiguez, et al., "NFAT5, a constitutively nuclear NFAT protein that does not cooperate with Fos and Jun", PNAS, 96:7214-7219 (1999).
Ouk, et al., "Direct Rel/NF-κB inhibitors: structural basis for mechanism of action", Future Med. Chem., 1(9):1683-1707 (2009).
Rouffet, et al., "From sensors to silencers: Quinoline- and benzimidazole-sulfonamides as inhibitors for zinc proteases", JACS, 132:8232-8233 (2010).
Tsai, et al., "The first pharmacophore model for potent NF-κB inhibitors", Bioorganic & Medicinal Chemistry Letters, 19:5665-5669 (2009).
Xie, et al., "Convenient preparation of N-8-quinolinyl benzenesultams as novel NF-κB inhibitors", Tetrahedron Letters, 49:2320-2323 (2008).

(Continued)

*Primary Examiner* — Layla Soroush
(74) *Attorney, Agent, or Firm* — Baker Botts L.L.P.

(57) ABSTRACT

The present invention relates to the NQBS class of molecules. It is based, at least in part, on the discovery that a representative group of compounds have been observed to inhibit nuclear translocation of NF-κB subunits. Without being bound by any particular theory, this inhibition of nuclear translocation may be mediated by either (i) binding of the NQBS or related compound to the C-terminus of the RHD, which specifically mediates the nuclear internalization; or (ii) NQBS-mediated stabilization of the dimer/IκB complex, disallowing dissociation of the active NF-κB monomers, and thus, inhibiting the generation of the subunits necessary to enter the nucleus. The NQBS class of molecules, and related molecules, may be used in therapeutic applications where inhibition of NF-κB translocation is beneficial, including but not limited to the treatment of cancer, autoimmune disorders, and inflammatory states.

2 Claims, 41 Drawing Sheets

(56) References Cited

FOREIGN PATENT DOCUMENTS

Figure 1A:
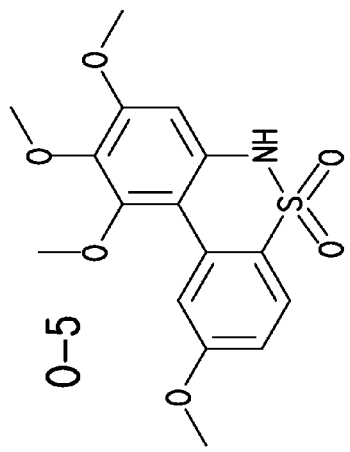
Figure 1C:
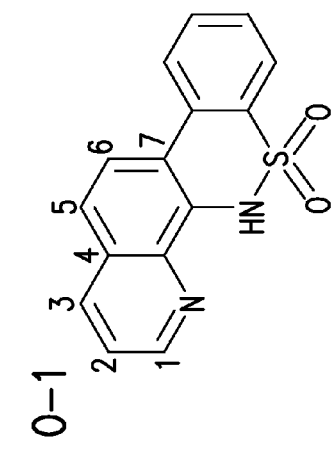
Figure 1B:
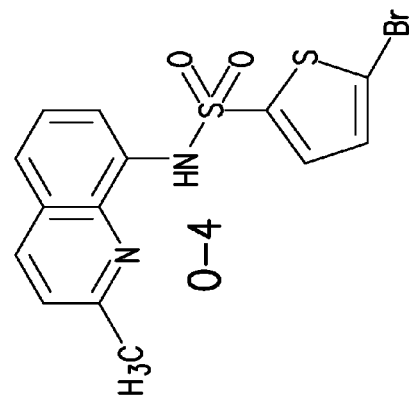
Figure 1D:
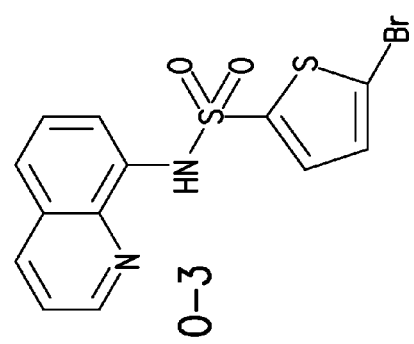
Figure 1E:
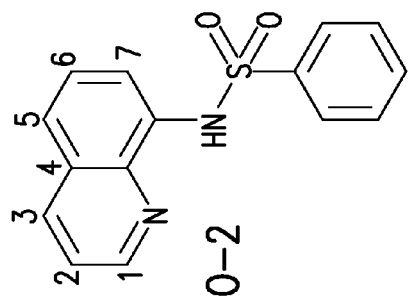

| WO | WO 2010/051064 | 5/2010 |
|---|---|---|
| WO | WO 2012/110603 | 8/2012 |

OTHER PUBLICATIONS

Xie, et al., "Identification of N-(quinolin-8-yl) benzenesulfonamides as agents capable of down-regulating NFκB activity within two separate high-throughput screens of NFκB activation", Bioorganic & Medicinal Chemistry Letters, 18:329-335 (2008).

Xie, et al., "Small-molecule modulators of the NF-κB pathway newly identified by a translocation-based cellular assay", Current Topics in Medicinal Chemistry, 9(13):1172-1180 (2009).

Everson da Silva, et al., 4-Fluoro-N-(quinolin-8-yl)benzenesulfonamide, Acta. Cryst. (2005) E61, o4387-o4388.

Hirayama, et al., "Substituent on Benzenesulfonyl Group" Effect in Use of 8-Benzenesulfonamideoquinoline Derivatives as Chelate Extractant, Analytical Sciences, Feb. 2003, vol. 19, pp. 321-324.

Almela, et al., "Copper(II) extraction by 4-chloro-N-8-quinolinylbenzenesulfonamide dissolved in toluene", J Chem Technol Biotechnol, 79:299-305 (2004).

Pagani, et al. Attivita Antimicrobica Di Chelanti Bidentati 8-Aminochinolinici, Il Farmaco Ed. Sc., vol. 26, Fasc. 2, pp. 118-131.

Crosby, et al., "Targeting hepcidin with antisense oligonucletides improves anemia endpoints in mice", Blood, American Society of Hematology, Nov. 1, 2006, vol. 108, No. 11, Part 1, pp. 83A-84A.

Da Silva, et al., "Synthesis and in vitro evaluation of leishmanicidal and trypanocidal activities of N-quinolin-8-yl-arylsulfonamides", Bioorganic & Medicinal Chemistry, Oct. 17, 2007, vol. 15, No. 24, pp. 7553-7560.

Liao Rong-Xia, et al., "[Experimental study on transcription regulation of mouse hepcidin gene by NF-κB]", Zhonghua Gan Zang Bing Za Zhi = Zhonghua Ganzangbing Zazhi = Chinese Journal of Hepatology, Feb. 2006, LNKD-PubMed:16494782, vol. 14, No. 2, pp. 118-123.

Pietrangelo, et al., "Hepcidin in human iron disorders: Therapeutic implications", Journal of Hepatology, Jan. 1, 2011, vol. 54, No. 1, pp. 173-181.

Sow Fatoumata B., et al., "Role of STAT1, NF-kappaB, and C/EBPbeta in the macrophage transcriptional regulation of hepcidin by mycobacterial infection and IFN-gamma", Journal of Leukocyte Biology, Nov. 2009, vol. 86, No. 5, pp. 1247-1258.

Buchwald et al., "Long-term, continuous intravenous heparin administration by an implantable infusion pump in ambulatory patients with recurrent venous thrombosis," Surgery, 88(4):507-516 (1980).

Burgess et al., "Analysis of gluconeogenic pathways in vivo by distribution of 2H in plasma glucose: comparison of nuclear magnetic resonance and mass spectrometry," Analytical Biochemistry, 318:321-324 (2003).

Chai et al., "Metal-mediated inhibition is a viable approach for inhibiting cellular methionine aminopeptidase," Bioorganic & Medicinal Chemistry Letters, 19:6862-6864 (2009).

During et al., "Controlled Release of Dopamine from a Polymeric Brain Implant: In Vivo Characterization," Ann Neurol., 25:351-356 (1989).

Goodson, Medical Applications of Controlled Release, vol. II Applications and Evaluation, Chapter 6, CRC Press Inc., Boca Raton, 115-138 (1984).

Howard et al., "Intracerebral drug delivery in rats with lesion-induced memory deficits," J. Neurosurg., 71:105-112 (1989).

Langer et al., "Chemical and Physical Structure of Polymers as Carriers for Controlled Release of Bioactive Agents: A Review," Journal of Macromolecular Science, Part C, 23:61-126 (1983).

Langer, "New Methods of Drug Delivery," Science, 249:1527-1533 (1990).

Levy et al., "Inhibition of Calcification of Bioprosthetic Heart Valves by Local Controlled-Release Diphosphonate," Science, 228:190-192 (1985).

Perkins, "Integrating cell-signalling pathways with NF-κb and IKK function," Nat. Rev. Mol. Cell Biol. 8:49-62 (2007).

Saudek et al., "A Preliminary Trial of the Programmable Implantable Medication System for Insulin Delivery," NEJM, 321(9):574-579 (1989).

Sefton, CRC Crit. Rev. Biomed. Eng., 14(3):201-240 (1987).

Silva et al., "4,5-Dibromo-N-(8-quinolyl)thiophene-2-sulfonamide," Acta Cryst. Structure Reports Online, E62:o309-o310 (2006).

Growth Inhibition IC50 Values (μM) Calculated with Calcusyn Software Across DLBCL and HUVEC Lines for O-1 and O-4 – Luminescence Assays

| Cell Line | O-1 (μM) (Closed Ring Structure) | | | O-4 (μM) (Open Ring Structure) | | |
|---|---|---|---|---|---|---|
| | 24h | 48h | 72h | 24h | 48h | 72h |
| Ly1 (GCB) | 5.31 | 2.96 | 3.7 | 2.1 | 1.4 | 1.4 |
| Ly7 (GCB) | 3.29 | 2.02 | 1.67 | 4.01 | 3.44 | 3.3 |
| Ly10 (ABC) | 4.56 | 5.64 | 1.5 | 1.6 | 1.6 | 1.5 |
| HBL-1 (ABC) | >10 | 6.2 | 5.7 | 3.09 | 2 | 3.42 |
| RIVA (ABC) | 8.29 | 4.29 | 2.88 | 6.95 | 4.1 | 2.72 |
| SUDHL6 (GCB) | 7.42 | 4.49 | 3.97 | 4.29 | 4.01 | 4.79 |
| HUVEC | >10 | >10 | 6.74 | >10 | >10 | >10 |

FIG. 2

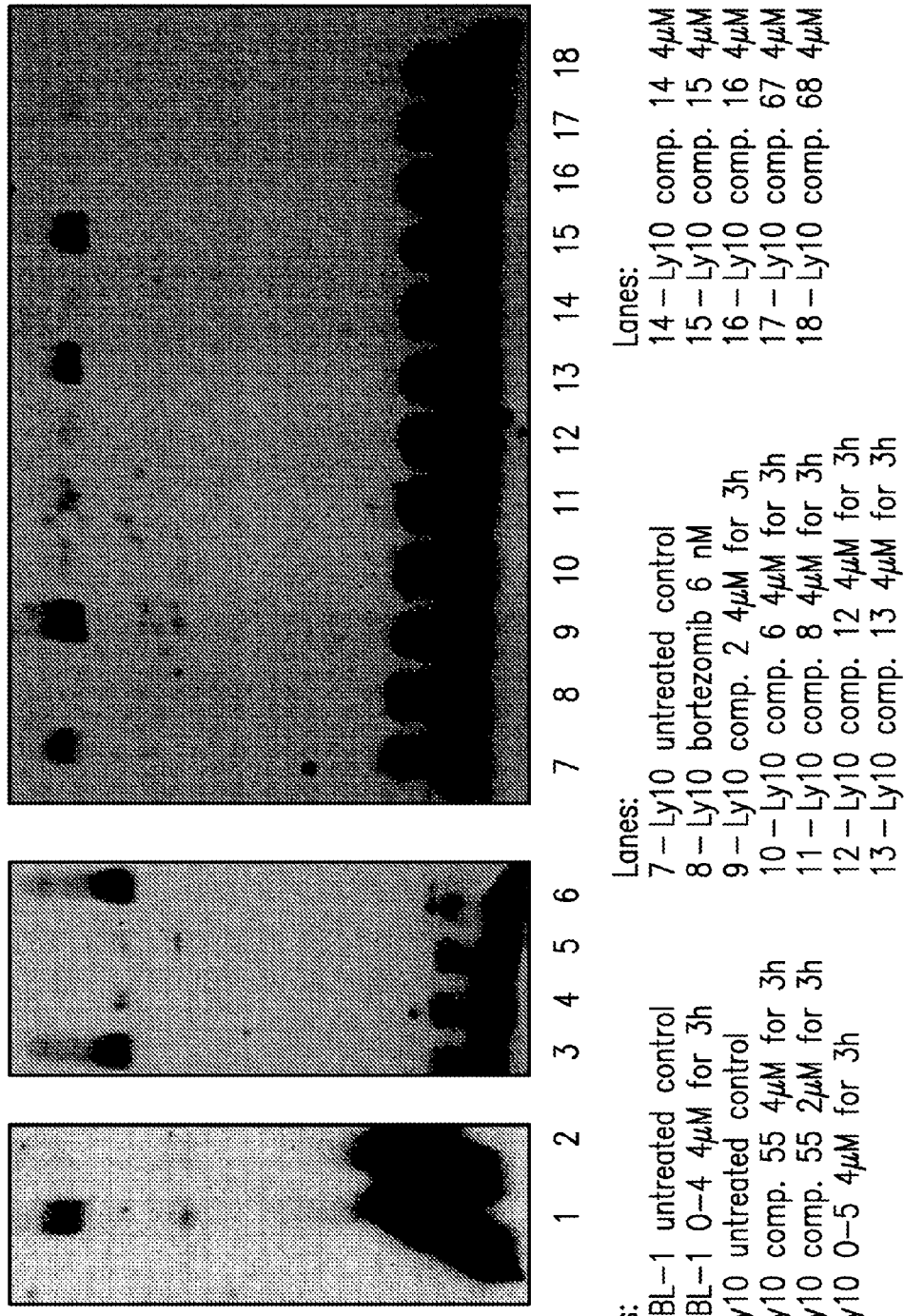

NQBS analogs – summary

| Compound No. | Chemical Structure | IC50 (μM) Ly1/Ly10 | Likely orally active (Lipinski) | ICM binding | EMSA | IF |
|---|---|---|---|---|---|---|
| 1 | 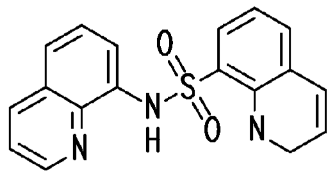 | 10–20/10–20 | yes | | | |
| 2 | 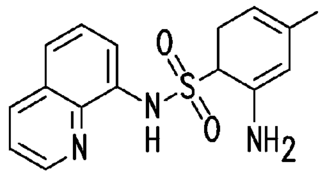 | 2.4/2.3 | yes | Site 2 | – | |
| 3 | 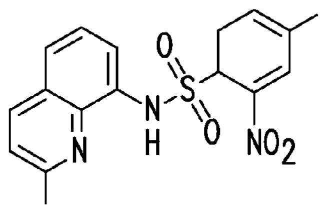 | >100/>100 | yes | | | |
| 4 | 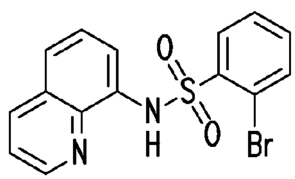 | 10–20/10–20 | yes | | | |

FIG. 8A

| | | | | | |
|---|---|---|---|---|---|
| | | | | + | |
| | | | Site 3 | | |
| 5 | 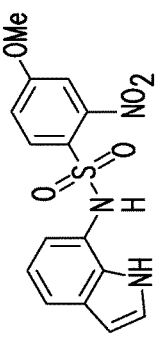 | 10–20/10–20 | yes | Site 3 | |
| 6 | 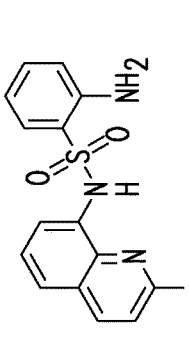 | 1.7/1.6 | yes | | + |
| 7 | 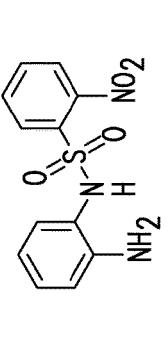 | >100/>100 | yes | Site 1 | |
| 8 | 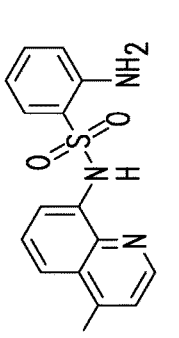 | 1.9/2.8 | yes | Site 2 | + |
| 9 | 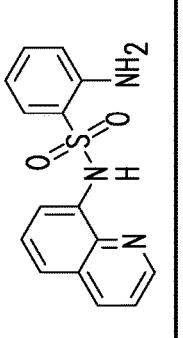 | 10–20/10–20 | yes | Site 1 | |
FIG. 8B

| | | | | |
|---|---|---|---|---|
| 10 | ![structure: 4-chlorophenyl sulfonamide of 2-nitrobenzene] | 20-50/20-50 | yes | Site 2 and 3 | |
| 11 | ![structure: 3,4,5-trimethoxyphenyl sulfonamide of 4-methoxy-2-aminobenzene] | 5.1/1.5 | yes | | + |
| 12 | ![structure: quinolin-8-yl sulfonamide of 4-methoxy-2-amino-methylbenzene] | 1.3/1.2 | yes | Site 3 | + |
| 13 | ![structure: quinolin-8-yl sulfonamide of 4-CF3-2-aminobenzene] | 1.5/1.4 | yes | | − |

FIG. 8C

| | | | | | |
|---|---|---|---|---|---|
| 14 | ![structure with OMe, NO2, sulfonamide, methylquinoline] | 2.4/2.1 | yes | Site 2 | + |
| 15 | ![structure with OMe, NH2, sulfonamide, quinoline] | 7.2/7.7 | yes | Site 1 | – |
| 16 | ![structure with NO2, sulfonamide, quinoline] | 1.9/1.5 | yes | Site 3 | + |
| 17 | ![structure with Br substituents, sulfonamide, quinoline] | 20/10–20 | no | | |

FIG. 8D

| | | | | | |
|---|---|---|---|---|---|
| 18 | 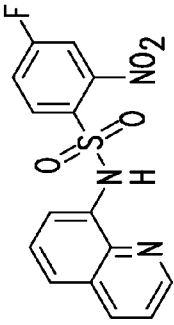 | 1.7/1.6 | yes | Site 2 | |
| 19 | 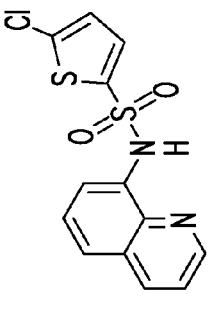 | 0.8/0.7 | yes | Site 3 | + |
| 20 | 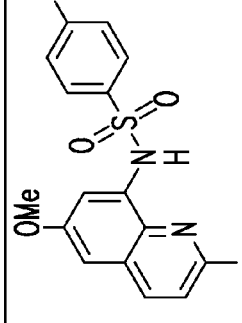 | 20-50/20-50 | yes | Site 2 | |
| 21 | 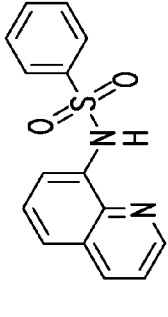 | 10-20/10-20 | yes | No | |
FIG. 8E

| | | | | |
|---|---|---|---|---|
| | | | | + |
| | Site 1 | Site 2 | Site 3 | |
| | yes | yes | yes | yes |
| | 2.6/2.3 | 20/10–20 | 1.3/1.2 | 1.3/0.8 |
| 22 | [structure: OMe-quinoline-NH-SO2-methyl-NO2-phenyl] | | | |
| 23 | | [structure: Cl-phenyl-NH-SO2-phenyl-NH2] | | |
| 24 | | | [structure: methylquinoline-NH-SO2-F-phenyl-NH2] | |
| 25 | | | | [structure: methylquinoline-NH-SO2-Cl-thiophene] |

FIG. 8F

| | | | | |
|---|---|---|---|---|
| | | | +/− | |
| | | Site 1 | | |
| 26 | [structure: CF3-substituted benzenesulfonamide with NH2, linked to 2-methylquinolin-8-yl] | 1.4/1.3 | yes | Site 1 |
| 27 | [structure: p-tolyl sulfonamide linked to 6-methoxyquinolin-8-yl] | 1.6/1.6 | yes | |
| 28 | [structure: OMe-substituted benzenesulfonamide with NH2, linked to quinolin-8-yl] | 1.4/0.8 | yes | Site 3 |
| 29 | [structure: 4-F, 2-NO2 benzenesulfonamide linked to 2-methylquinolin-8-yl] | 1.9/1.5 | yes | Site 1 |

FIG. 8G

| | | | | |
|---|---|---|---|---|
| 30 | 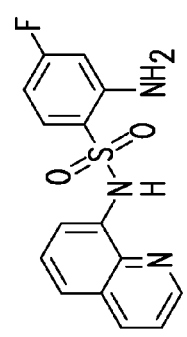 | 1.4/1.5 | yes | Site 1 | – |
| 31 | 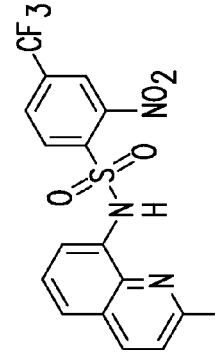 | 3.2/3.0 | yes | Site 2 | +/– |
| 32 | 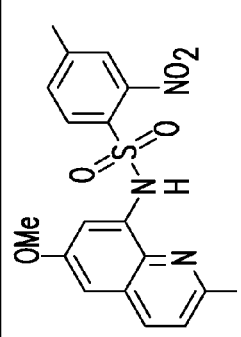 | 10–20/10–20 | yes | Site 2 | |
| 33 | 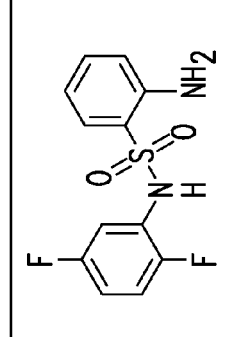 | 20/10–20 | yes | Site 2 | |
FIG. 8H

| | | | | |
|---|---|---|---|---|
| 34 | ![structure with OMe, NH2, methyl, methoxyquinoline sulfonamide] | 1.2/1.0 | yes | Site 1 | +/− |
| 35 | ![structure with OMe, NO2, quinoline sulfonamide] | 3.2/2.8 | yes | Site 2 | − |
| 36 | ![structure with NO2, Br, phenyl sulfonamide] | 10-20/10-20 | yes | No | |
| 37 | ![structure with methylquinoline, quinoline sulfonamide] | 20-50/20-50 | yes | Site 1 | |

FIG. 8I

| | | | | |
|---|---|---|---|---|
| 38 | (structure with SO2NH linker, phenyl-NH2 and phenyl-NHAc) | >100/>100 | yes | Site 3 | |
| 39 | (structure with SO2NH linker, phenyl-NHOH and dihydroquinoline) | 3.5/1.3 | yes | Site 3 | + |
| 40 | (structure with SO2NH linker, OMe/NH2 phenyl and indole-NH) | 5.0/1.2 | yes | Site 1 | + |
| 41 | (structure with SO2NH linker, Cl/NO2 phenyl and quinoline) | 4.1/5.8 | yes | | − |

FIG. 8J

| ID | Structure | Ratio | | Site | | |
|---|---|---|---|---|---|---|
| O-4 (42) | (structure) | 1.4/1.5 | yes | Sites 1 and 3 | + | + |
| O-1 (43) | (structure) | 3.7/1.5 | yes | Site 1 | + | + |
| O-2 (44) | (structure) | 1.7/1.7 | yes | Site 1 | | + |
| O-3 (45) | (structure) | 1.4/1.4 | yes | Site 1 | | + |

FIG. 8K

| | | | | | | |
|---|---|---|---|---|---|---|
| 0-5 (46) | [structure: trimethoxybiphenyl sulfonamide] | >100/>100 | yes | No | — | — |
| 47 | [structure: 4,5-dichlorothiophene-2-sulfonamide-quinolin-8-yl] | 0.7/0.7 | yes | | | |
| 48 | [structure: 5-chloro-4-nitrothiophene-2-sulfonamide-quinolin-8-yl] | 10-20/10-20 | yes | | | |
| 49 | [structure: 4,5-dibromothiophene-2-sulfonamide-quinolin-8-yl] | 1.4/1.5 | yes | | | |

FIG. 8L

| | | | | | |
|---|---|---|---|---|---|
| 50 | 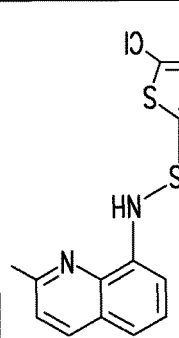 | 10-20/10-20 | yes | | |
| 51 | 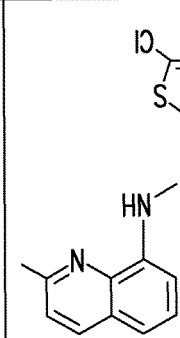 | 10-20/10-20 | yes | | |
| 52 | 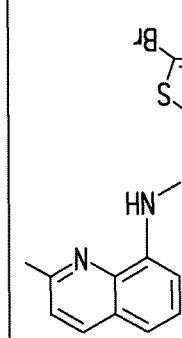 | 10-20/10-20 | yes | | |
| 53 | 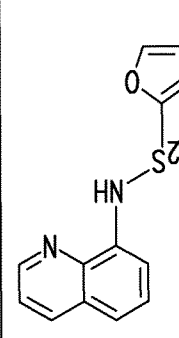 | 20-50/20-50 | yes | | |
FIG. 8M

| | | | | |
|---|---|---|---|---|
| | | | + | |
| | | | | |
| | | yes | yes | yes | yes |
| | | 6.3/5.4 | 0.5/0.5 | 10-20/10-20 | 1.7/3.1 |
| 54 | | | | |
| 55 | | | | |
| 56 | | | | |
| 57 | | | | |

FIG. 8N

| | | | | | | |
|---|---|---|---|---|---|---|
| 58 | 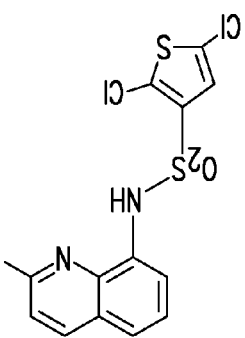 | 1.4/2.6 | yes | | + | |
| 59 | 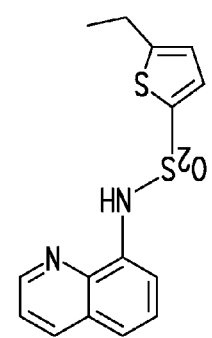 | 1.4/2.6 | yes | | + | |
| 60 | 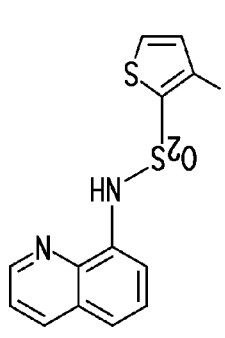 | 1.3/2.6 | yes | | + | |
| 61 | 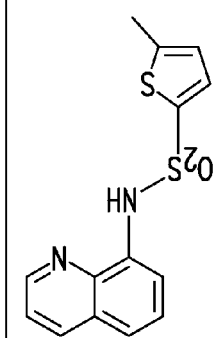 | 1.1/2.4 | yes | | + | |
FIG. 8O

| | | | | |
|---|---|---|---|---|
| 62 | ![structure: 8-quinolinyl sulfonamide with thiazole] | 20-50/20-50 | yes | |
| 63 | ![structure: 8-quinolinyl sulfonamide with pyridine] | 10-20/10-20 | yes | |
| 64 | ![structure: 2-methyl-8-quinolinyl sulfonamide with 5-ethylthiophene] | 1.6/3.2 | yes | I |
| 65 | ![structure: 2-methyl-8-quinolinyl sulfonamide with 3-methylthiophene] | 10-20/10-20 | yes | |

FIG. 8P

| | | | | |
|---|---|---|---|---|
| 66 | 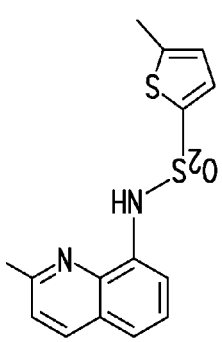 | 0.6/1.7 | yes | | + |
| 67 | 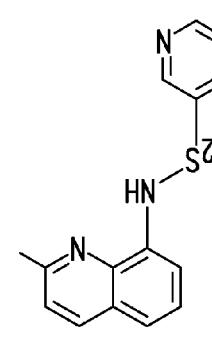 | 1.3/1.8 | yes | | + |
| 68 | 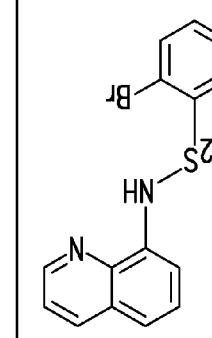 | 1.5/1.2 | yes | | + |
| 69 | 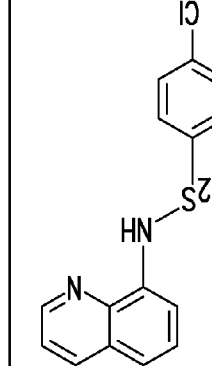 | 0.7/0.7 | yes | | + |
FIG. 8Q

| | | | | |
|---|---|---|---|---|
| 70 | 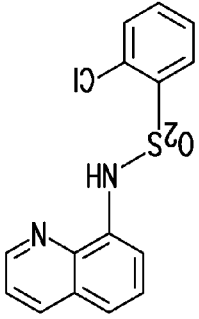 | 1.1/1.2 | yes | + |
| 71 | 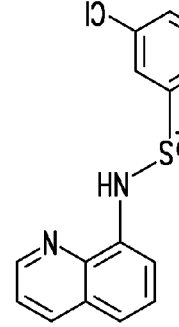 | 1.2/1.2 | yes | + |
| 72 | 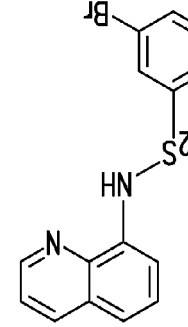 | 1.9/1.5 | yes | – |
| 73 | 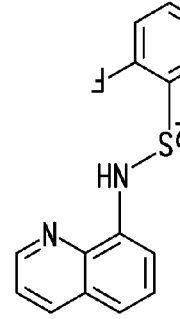 | 0.9/1.0 | yes | – |
FIG. 8R

| | | | | |
|---|---|---|---|---|
| 74 | 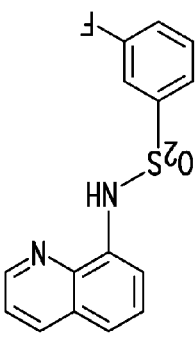 | 0.7/0.7 | yes | +/− |
| 75 | 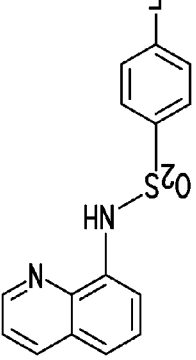 | 0.7/0.7 | yes | + |
| 76 | 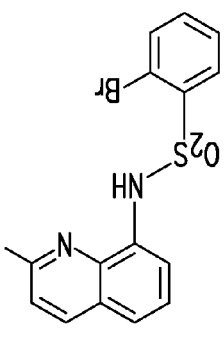 | 3.7/3.9 | yes | − |
| 77 | 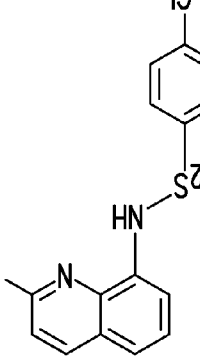 | 1.5/1.2 | yes | − |
FIG. 8S

| | | | |
|---|---|---|---|
| | | | |
| | | | |
| 78 | 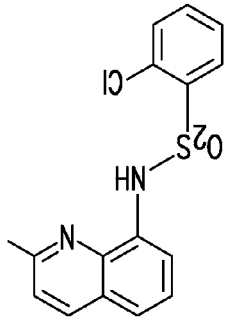 | 3.8/3.0 | yes |
| 79 | 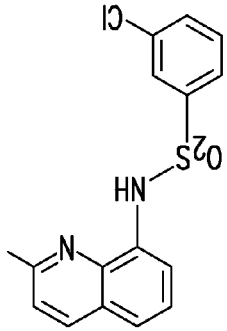 | 1.7/1.6 | yes |
| 80 | 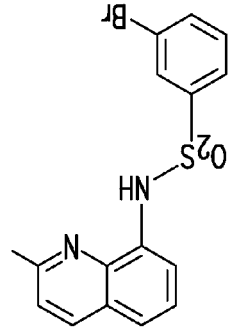 | 1.2/1.0 | yes |
| 81 | 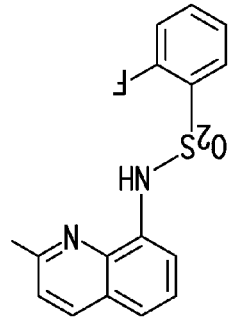 | 1.8/1.9 | yes |
FIG. 8T

| | | | |
|---|---|---|---|
| | | | |
| | | | |
| | yes | yes | yes | yes |
| | 1.5/1.0 | 1.5/1.1 | >100/20–50 | 50–100/20–50 |
| | 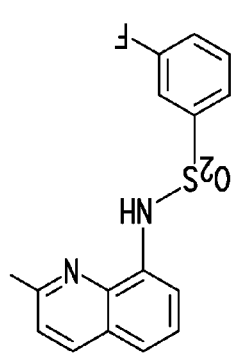 | 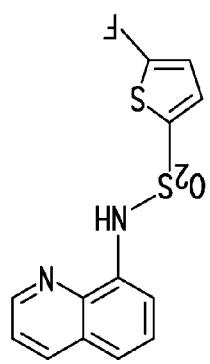 | 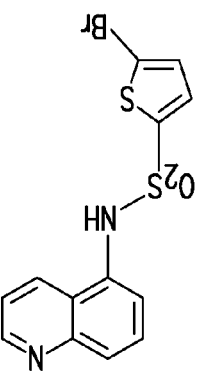 | 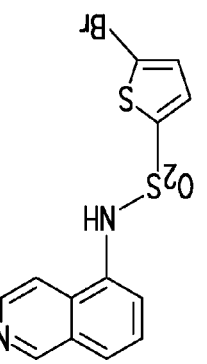 |
| | 82 | 83 | 84 | 85 |
FIG. 8U

| | | | | |
|---|---|---|---|---|
| 86 | 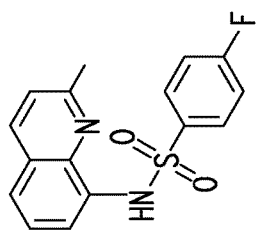 | 2.1/2.3 | yes | |
| 87 | 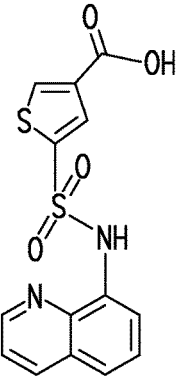 | >100/>100 | yes | |
| 88 | 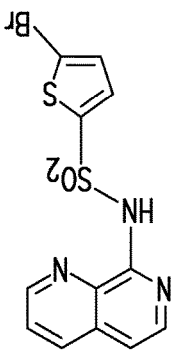 | 50/50–100 | yes | |
| 89 | 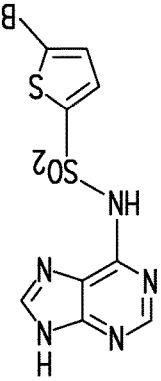 | >100/>100 | yes | |
FIG. 8V

| | | | | | | | |
|---|---|---|---|---|---|---|---|
| 90 | ![structure: N-(quinolin-8-yl)-5-methylfuran-2-sulfonamide] | 50-100/50-100 | | yes | | | |
| 91 | | | | | | | |
| 92 | | | | | | | |
| 93 | | | | | | | |
| 94 | | | | | | | |
| 95 | | | | | | | |
| 96 | | | | | | | |
| 97 | | | | | | | |

FIG. 8W

O-4 and C19 Also Demonstrate Significant Cytotoxicity in Solid Tumors

| Cell line | Origin | NF-κB constitutive activation | IC50 (μM) O-4 at 72h | IC50 (μM) C19 at 72h |
|---|---|---|---|---|
| DLD-1 myc +; myb +; ras +; fos +; sis +; p53 + | Colorectal adenocarcinoma | yes | 3.2 | 3.0 |
| SW480 myc +; myb +; ras +; fos +; sis +; p53 + | Colorectal adenocarcinoma | intermediate | 4.1 | 4.0 |
| LNCaP androgen sensitive | Prostate adenocarcinoma | no | 3.9 | 1.6 |
| PC-3 androgen sensitive | Prostate adenocarcinoma | yes | 4.1 | 4.0 |
| SKBR 3 HER2/c-erb-2 + | Breast adenocarcinoma | no | 9.9 | >10 |
| MDA231 Triple negative | Breast adenocarcinoma | yes | >10 | >10 |
| FM29 | Melanoma | unclear | 7.4 | 6.3 |
| M44 | Melanoma | unclear | 2.4 | 0.9 |
| SK19 | Melanoma | unclear | 8.1 | 2.3 |

FIG. 9

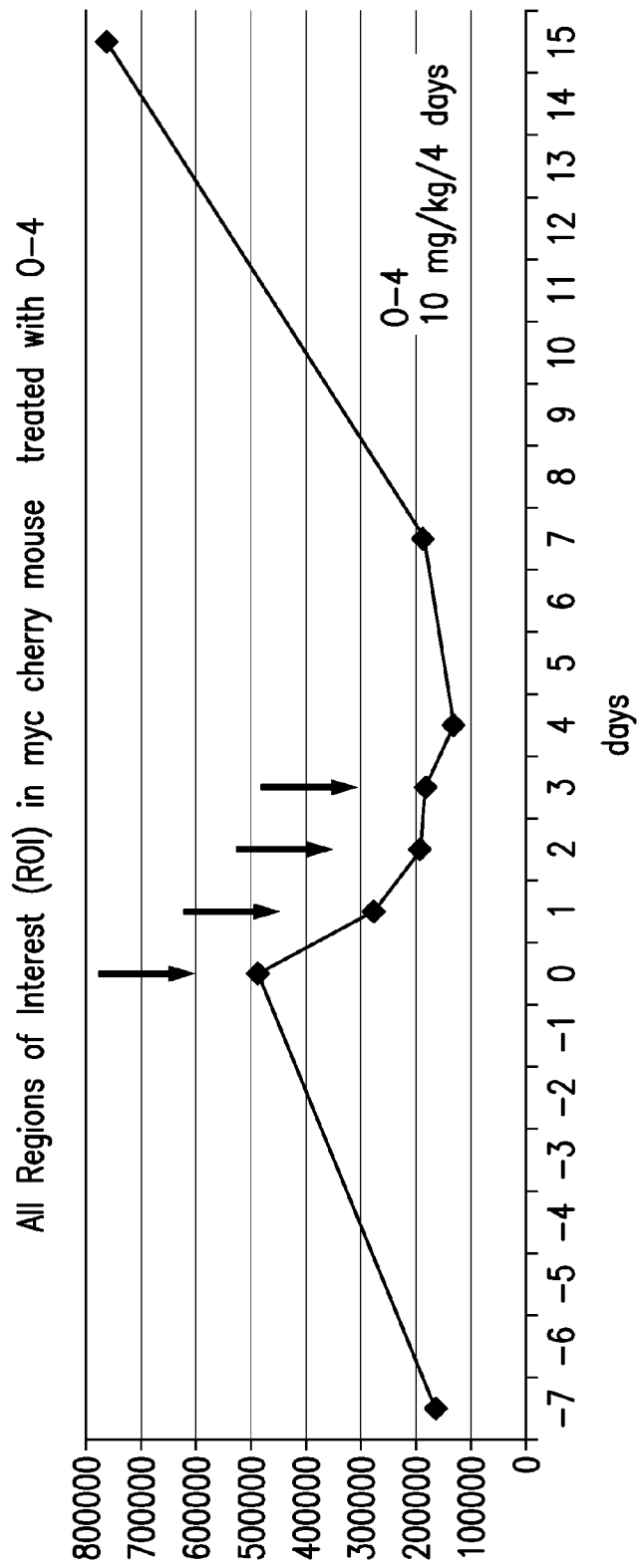

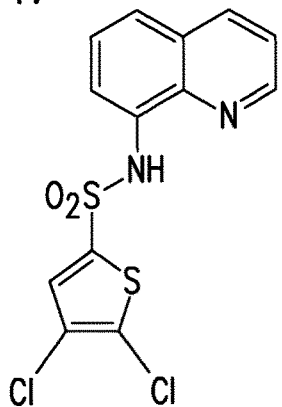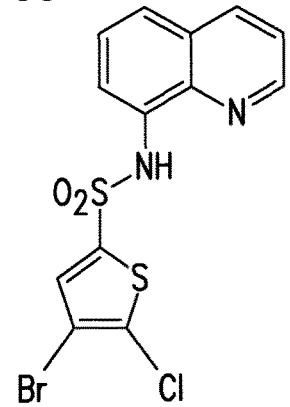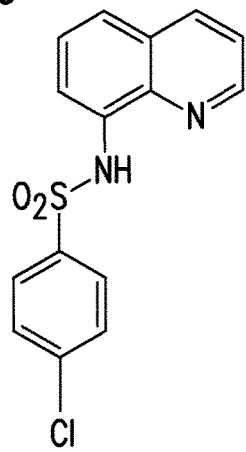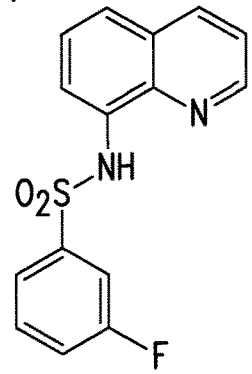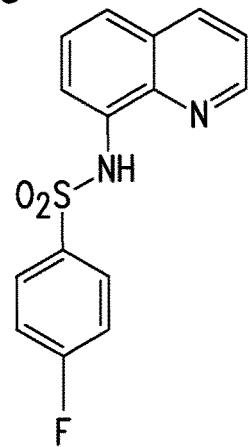
FIG. 14

US 9,896,420 B2

N-QUINOLIN-BENZENSULFONAMIDES AND RELATED COMPOUNDS FOR THE TREATMENT OF CANCER, AUTOIMMUNE DISORDERS AND INFLAMMATION

PRIORITY CLAIM

The present application is a continuation of International Application Serial No. PCT/US2012/028619, filed Mar. 9, 2012 and published in English as WO/2012/122534 on Sep. 13, 2012, which claims priority to U.S. Provisional Application Ser. No. 61/451,408, filed Mar. 10, 2011, the contents of each of which are incorporated by reference in their entireties herein, and to each of which priority is claimed.

GRANT INFORMATION

This invention was made with government support under grants HG003914, RR024156, AG008702, and AT002643 awarded by the National Institutes of Health. The government has certain rights in the invention.

SEQUENCE LISTING

The specification further incorporates by reference the Sequence Listing submitted herewith via EFS on Sep. 6, 2013. Pursuant to 37 C.F.R. § 1.52(e)(5), the Sequence Listing text file, identified as 0700504995Seqlist.txt, is 3,107 bytes and was created on Sep. 5, 2013. The Sequence Listing, electronically filed herewith, does not extend beyond the scope of the specification and thus does not contain new matter.

1. INTRODUCTION

The present invention relates to N-(quinolin-8-yl) benzenesulfonamides ("NQBS") and related compounds and their use as agents for treating cancer, autoimmune disorders and inflammatory conditions.

2. BACKGROUND OF THE INVENTION

One of the most ubiquitously implicated transcription factors in all of carcinogenesis is nuclear factor-κB (NF-κB). NF-κB represents a family of five proteins (p105/50, p100/p52, c-Rel, RelA/p65 and RelB) that affect over 400 genes, many of which are important in the context of cancer cell growth and survival (Perkins, 2007, Nature Rev. Mol. Cell Biol. 8:40-62). Many of these gene activate genes that: promote cancer cell growth; inhibit those mechanisms responsible for cell cycle arrest; and promote resistance to cell death. All NF-κB members contain a Rel homology domain ("RHD"), an approximately 300 amino acid long residue, which is a highly conserved sequence (e.g. SEQ ID NO:1 from AF134870 and see Lopez-Rodriguez et al., 1999, Proc. Natl. Acad. Sci. 96:7214-7219) near their N terminus of the RHD. This domain is the site that mediates binding to DNA, dimerization with other NF-κB subunits, and nuclear localization. SEQ ID NO: 1 is a human sequence as follows:

LSQLTTDNKGNSKAGNGTLENQKGTGVKKSPMLCGQYPVKSEGKELKIVV

QPETQHRARYLTEGSRGSVKDRTQQGFPTVKLEGHNEPVVLQVFVGNDSG

RVKPHGFYQACRVTGRNTTPCKEVDIEGTTVIEVGLDPSNNMTLAVDCVG

-continued
ILKLRNADVEARIGIAGSKKKSTRARLVFRVNIMRKDGSTLTLQTPSSPI

LCTQPAGVPEILKKSLHSCSVKGEEEVFLIGKNFLKGTKVIFQENVSDEN

SWKSEAEIDMELFHQNHLIVKVPPYHDQHITLPVSVGIYVVTNAGRSHDV

QPFTYTPD.

In normal cells, following an activation signal from the surface of the cell, NF-κB subunits translocate to the nucleus where they exert their effect on gene transcription by binding to DNA. The ability to transactivate specific genes in DNA is absolutely dependent on the ability of the NF-κB subunits to enter the nucleus, the site of all DNA replication and transcription.

There are at least three known NF-κB activation pathways: (1) the canonical or classical pathway, which is an IκB dependent pathway activated by extracellular signals such as TNFα, IL-1 and LPS; (2) the non-canonical or alternative pathway, which is an IκB independent pathway activated by CD40/CD40L interaction, and (3) the atypical pathway, which is stimulated by various signals including genotoxic stress, hypoxia and ROS (Perkins, 2007, Nature Rev. Mol. Cell Biol. 8:40-62). Within the classical pathway, NF-κB transcription factors are sequestered in the cytoplasm in their inactive state by the IκB family of inhibitory proteins (IκBa, IκBβ, IκBe, p105/κ and p100/d). Upon an activation signal, IκB kinase (IKK) phosphorylates IκB, rendering it a substrate for ubiquitination and subsequent proteosome mediated degradation. Removal of the IκB allows for nuclear translocation of the NF-κB complex, and activation of its target genes (Perkins, 2007, Nature Rev. Mol. Cell Biol. 8:40-62).

In the alternative pathway, IKK directly phosphorylates p100 which in turn induces the processing of p100 to p52, which is then translocated to the nucleus with subsequent activation of the target genes. The atypical pathway can lead to NF-κB activation in a IKK independent way (hypoxia and ROS activate Tyr kinase) or an IKK dependent way (genotoxic stress). Over expression and constitutive activation of NF-κB is thought to be one of the central events leading to cancer. This biology, first described in normal lymphocytes, is thought to play a pivotal role in the formation of lymphomas.

Identifying pharmacologic strategies to inhibit the activation of target NF-κB genes has been a major pursuit for cancer research laboratories over the past 2 decades.

Over the years, select agents indirectly affecting NF-κB biology have been identified, as discussed below. These agents affect NF-κB biology by inhibiting IκB kinase, which inhibits the phosphorylation and subsequent degradation of IκB, or by inhibiting the proteasome, and thus the proteolytic degradation of IκB.

NF-κB promotes the dysregulated growth and survival of many cancers, including most lymphomas. Efforts to inhibit NF-κB over the years have been fraught with many challenges, not the least of which has been the development of relatively NF-κB non-specific agents. One such example is bortezomib (Velcade), a proteasome inhibitor touted as an NF-κB inhibitor which has been approved for the treatment of myeloma and mantle cell lymphoma. While bortezomib inhibits the degradation of IκB, it also affects more than 90% of the protein turnover in the cell, and thus affects virtually every important cellular process known. Clinically, while effective, the drug is neurotoxic and is associated with an irreversible painful neuropathy. Clearly, more specific NF-κB inhibitors are needed. To date, direct binding of NQBS to the target protein (p65 and p50) has not yet been described within published literature and therefore represents a novel mode of action for a drug that inhibits NF-κB pathway.

3. SUMMARY OF THE INVENTION

The present invention relates to the NQBS class of molecules and related compounds. It is based, at least in part, on the discovery that a representative group of compounds have been observed to inhibit nuclear translocation of NF-κB subunits. Without being bound by any particular theory, this inhibition of nuclear translocation may be mediated by either (i) binding of the NQBS compound to the C-terminus of the RHD, which specifically mediates the nuclear internalization; or (ii) NQBS-mediated stabilization of the NF-κB dimer/IκB complex, disallowing dissociation of the active NF-κB monomers, and thus, inhibiting the generation of the subunits necessary to enter the nucleus. The NQBS class of molecules may be used in therapeutic applications where inhibition of NF-κB translocation is beneficial, including but not limited to the treatment of cancer, autoimmune disorders, and inflammatory states.

4. BRIEF DESCRIPTION OF THE FIGURES

FIG. 1A-E. Compounds (A) O-1; (B) O-5; (C) O-2; (D) O-3; and (E) O-4. These are examples of NQBS compounds having the C7-locked (A) or C7-open (C-E) configurations.

FIG. 2. Growth inhibition IC50 values (micromolar; μM) calculated with Calcusyn Software across DLBCL and TNFα unstimulated HUVEC lines for O-1 and O-4 luminescence assays.

Figure 3A:
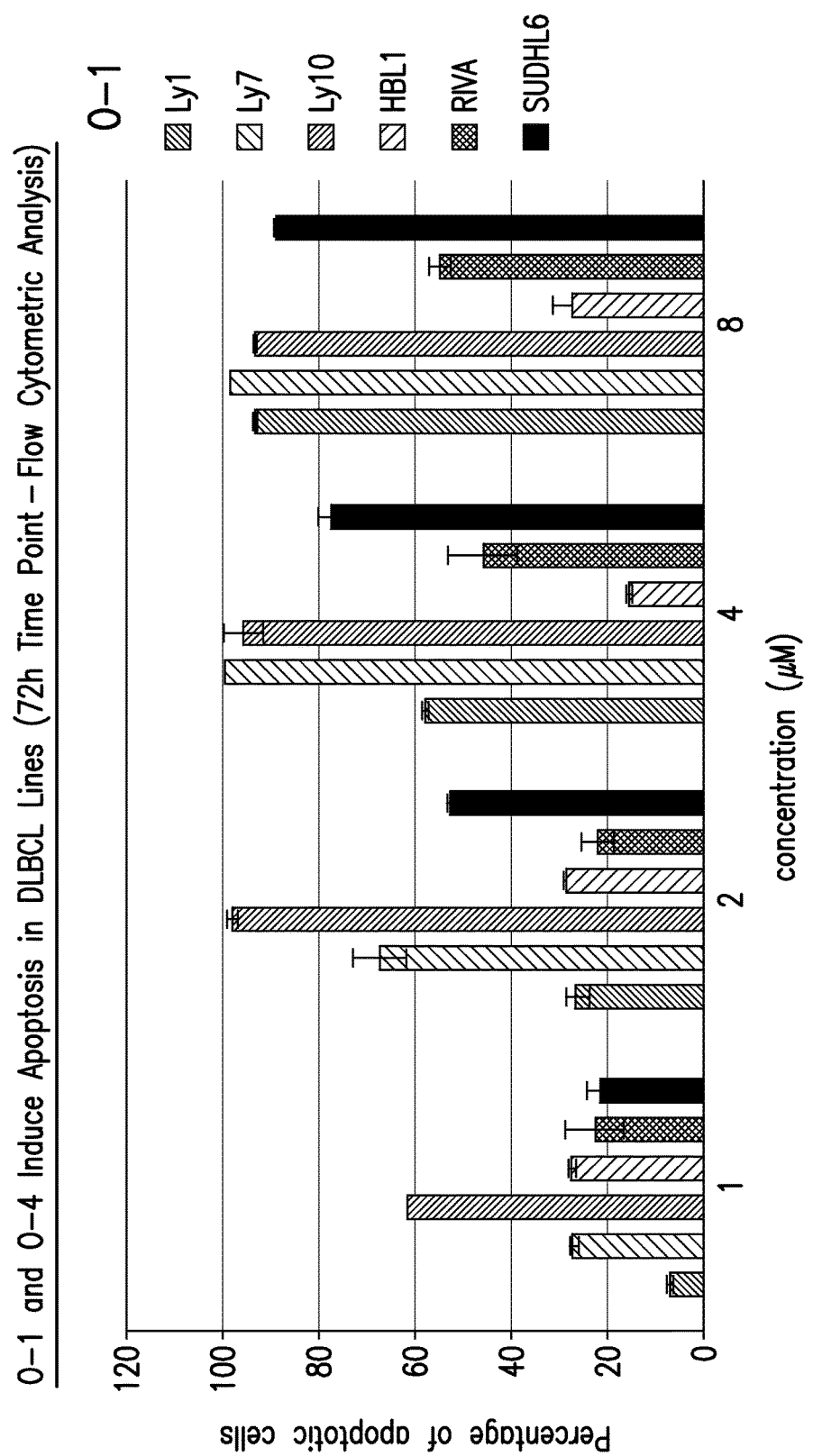

FIGS. 3A,B. Flow cytometric analysis showing percentage of apoptotic cells in DLBCL lines treated with (A) O-1 or (B) O-4 (72 hour time point).

Figure 4A:
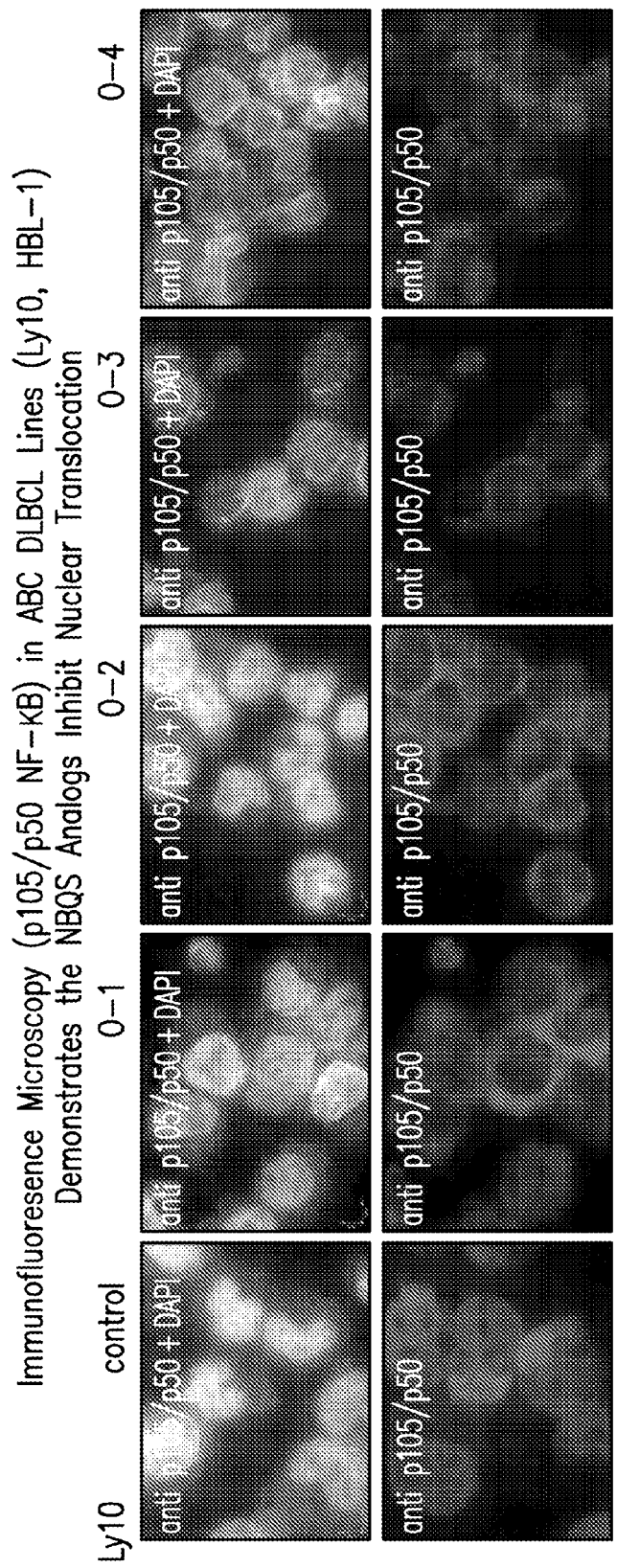
Figure 4B:
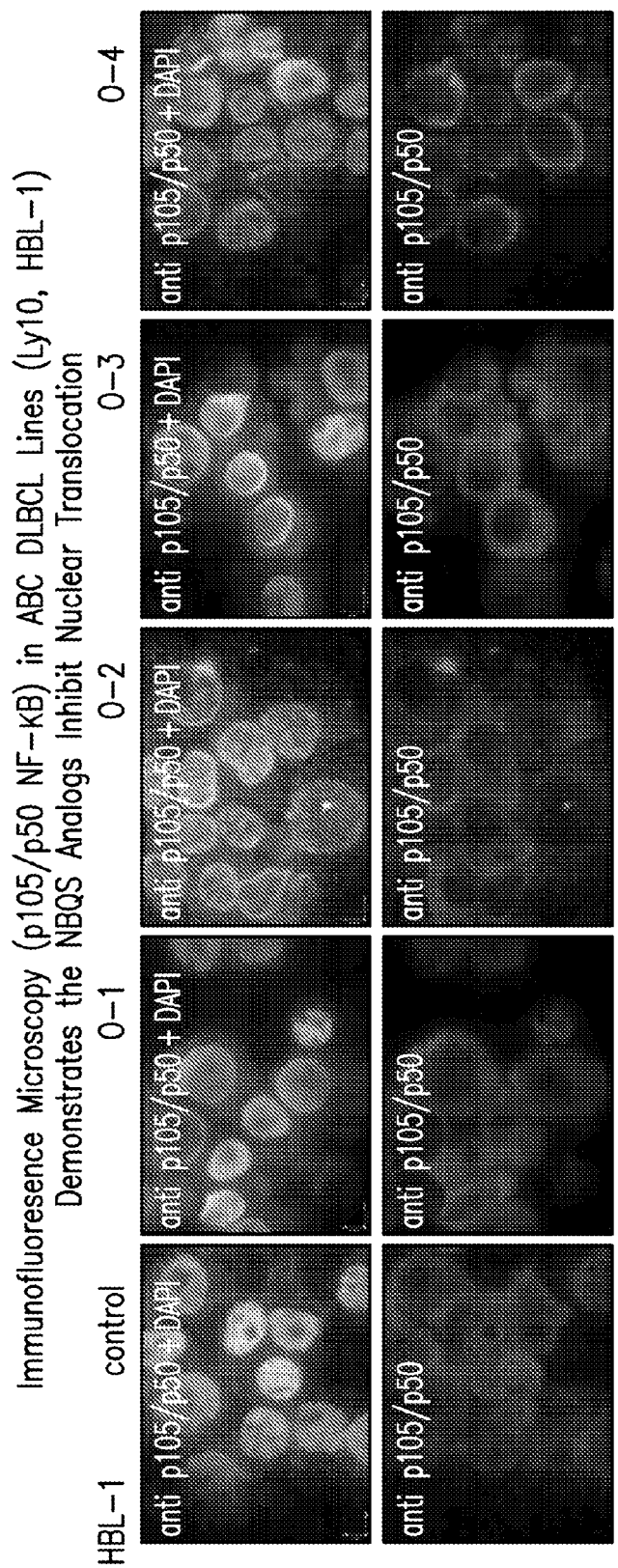

FIG. 4A-B. Laser confocal microscopy showing, via immunofluorescence of p105/p50 NF-κB), the effects of compounds O-1, O-2, O-3, and O-4, as compared to control, in either (A) Ly10 or (B) HBL-1 DLBCL cell lines.

FIG. 5. Nuclear NF-κB presence in HBL-1 (lanes 1 and 2) or Ly10 (lanes 3-18) DLBCL cell lines (EMSA), either untreated (lanes 1, 3 and 7) or treated with various compounds as indicated.

Figure 6:
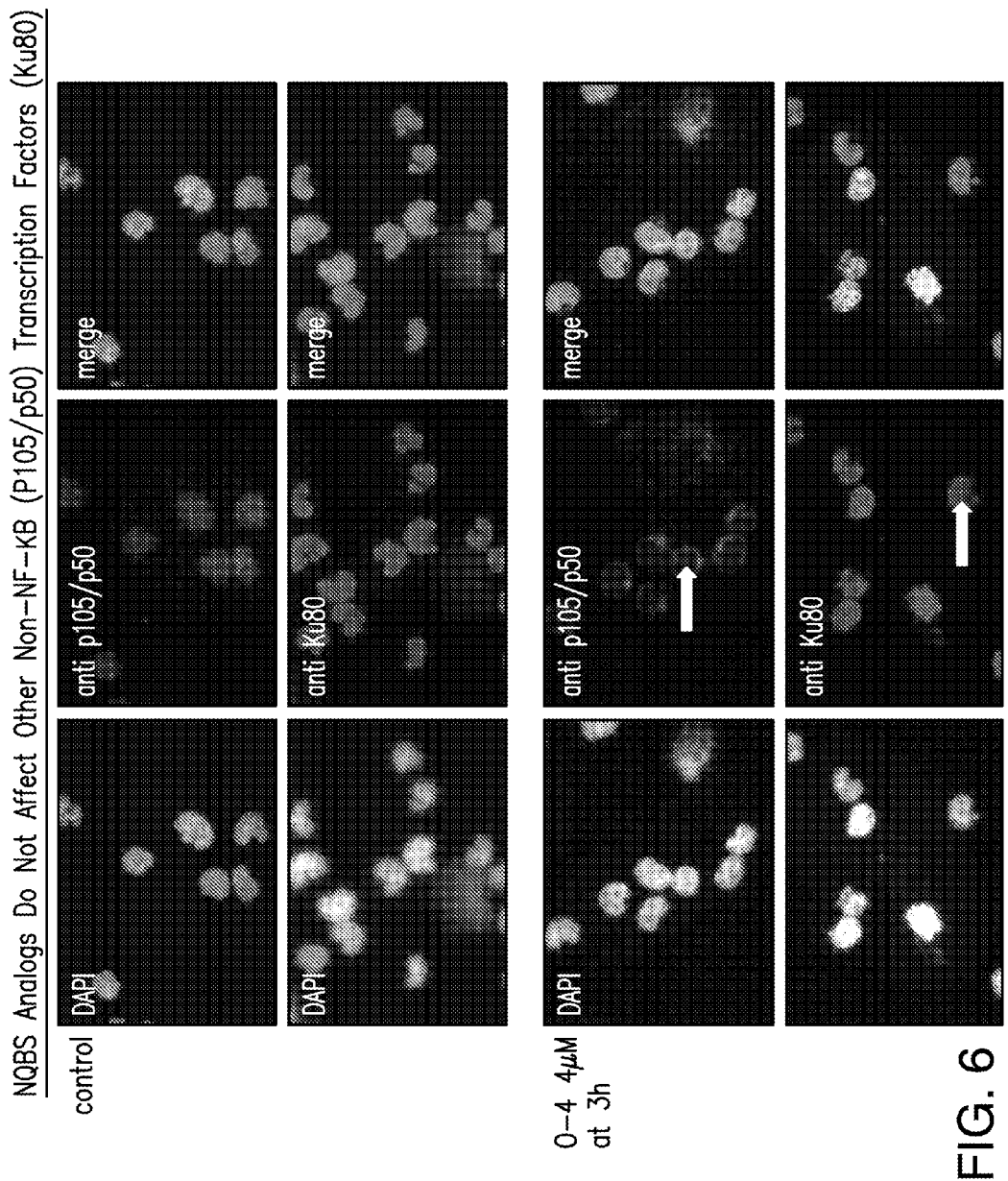

FIG. 6. Effect of NQBS compounds on transcription factors other than NF-κB.

Figure 7:
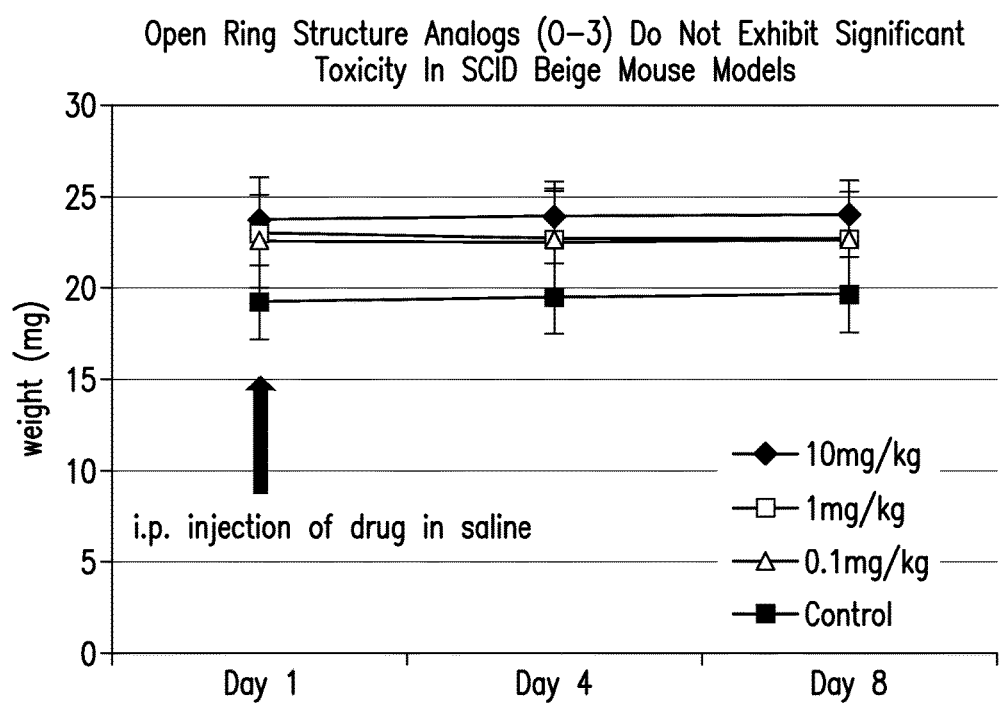

FIG. 7. Results of toxicity studies in SCID beige mice, as assessed by animal weight. Compound O-3 (an open-ring NQBS compound) was administered at doses of 10 mg/kg, 1 mg/kg, or 0.1 mg/kg.

FIG. 8A-W. Table summarizing all tested NQBS compounds with growth inhibition IC 50 values (luminescence assays) and EMSA and/or IF assay results for NF-κB translocation inhibition.

FIG. 9. Cytotoxicity of O-4 and O-19 toward solid tumors.

Figure 10:
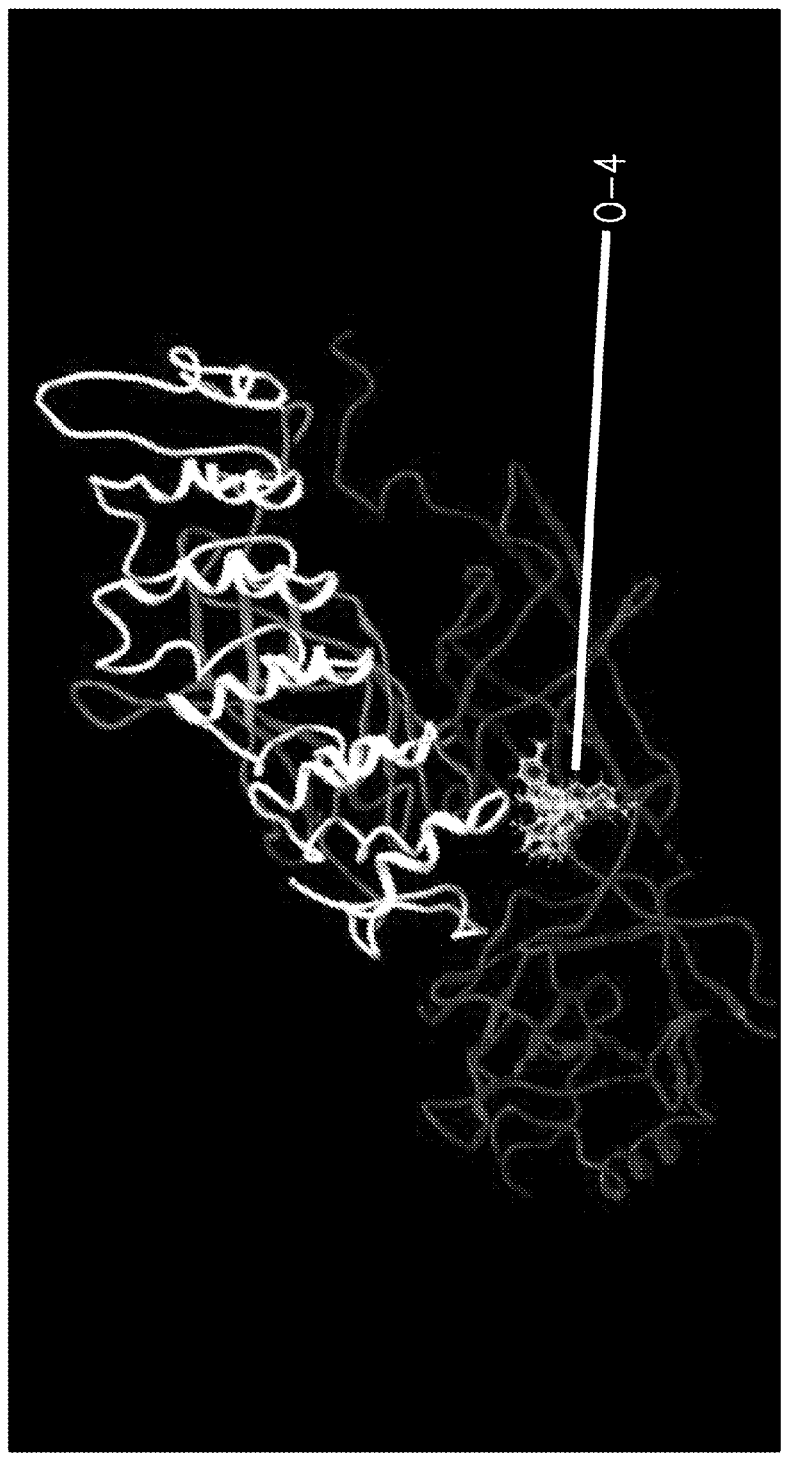

FIG. 10. Ribbon diagram showing association between O-4 and p65.

Figure 11A:
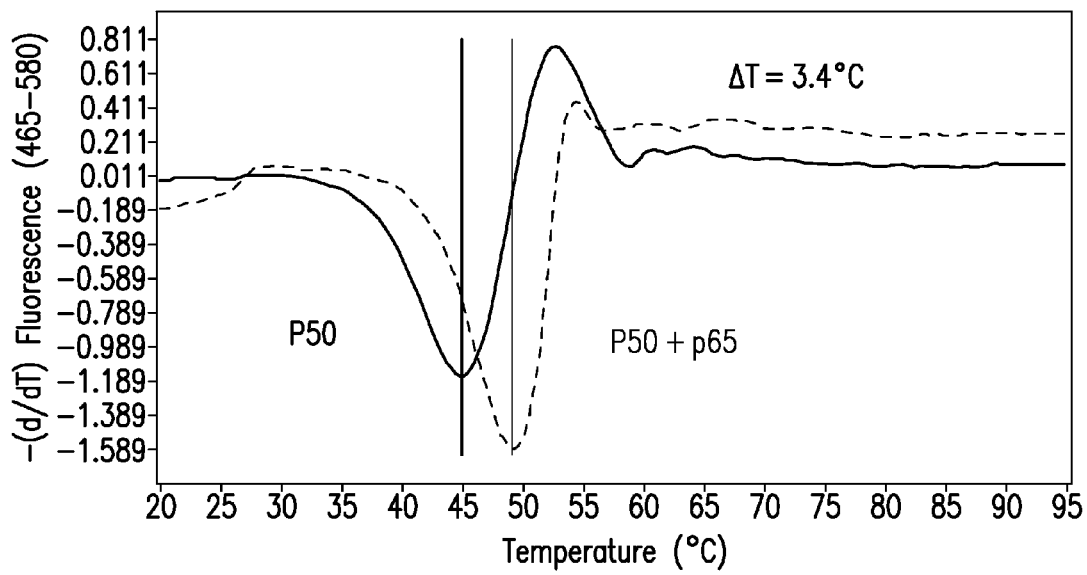
Figure 11B:
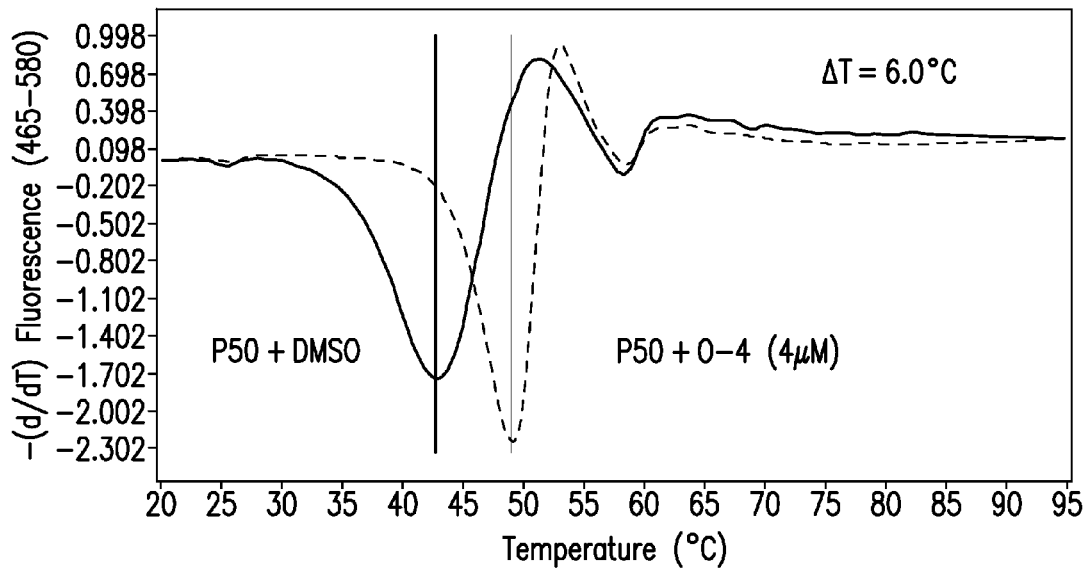
Figure 11C:
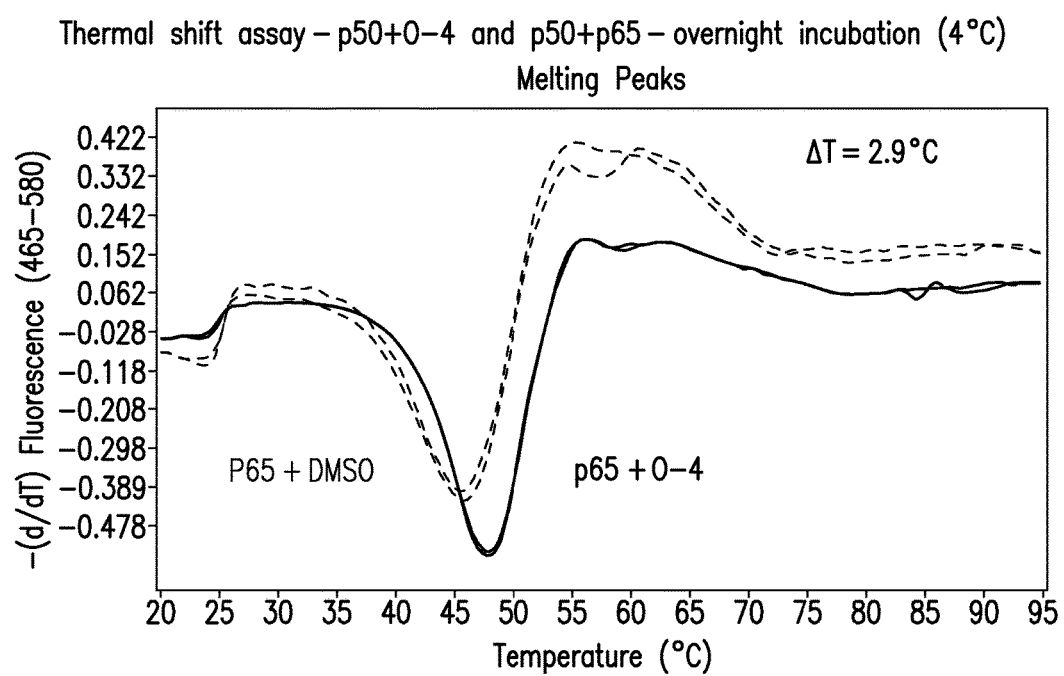
Figure 12A:
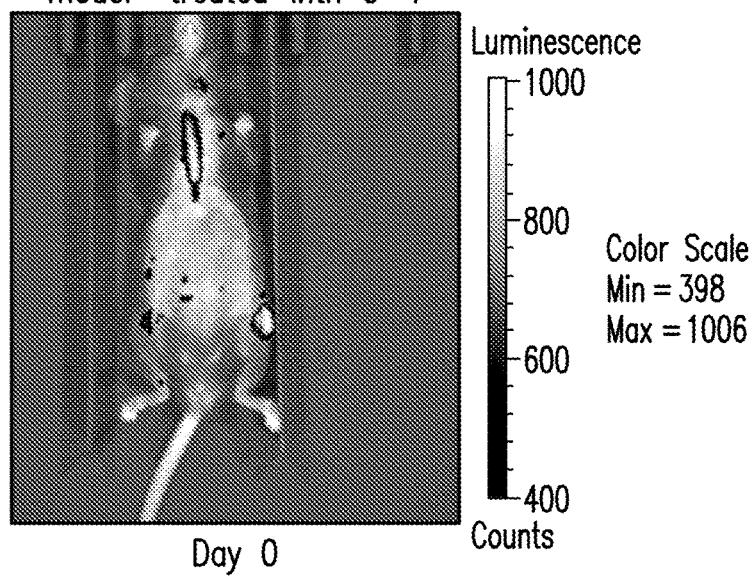
Figure 12B:
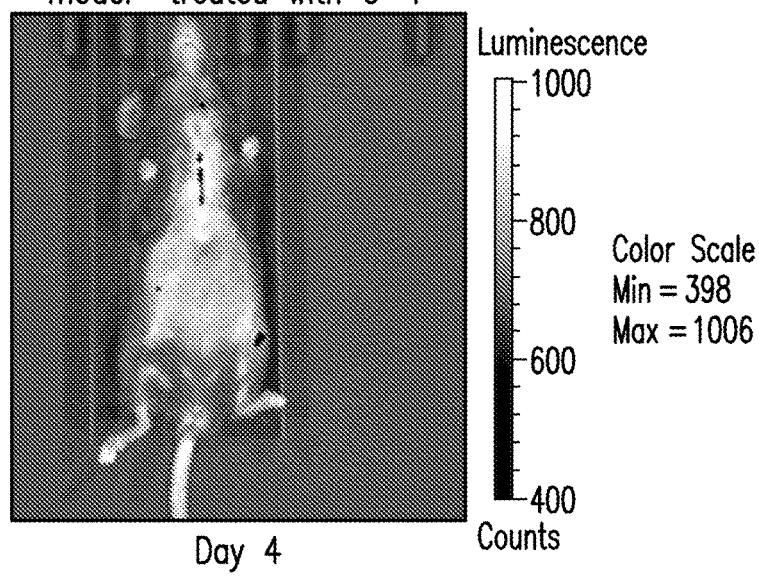
Figure 12C:
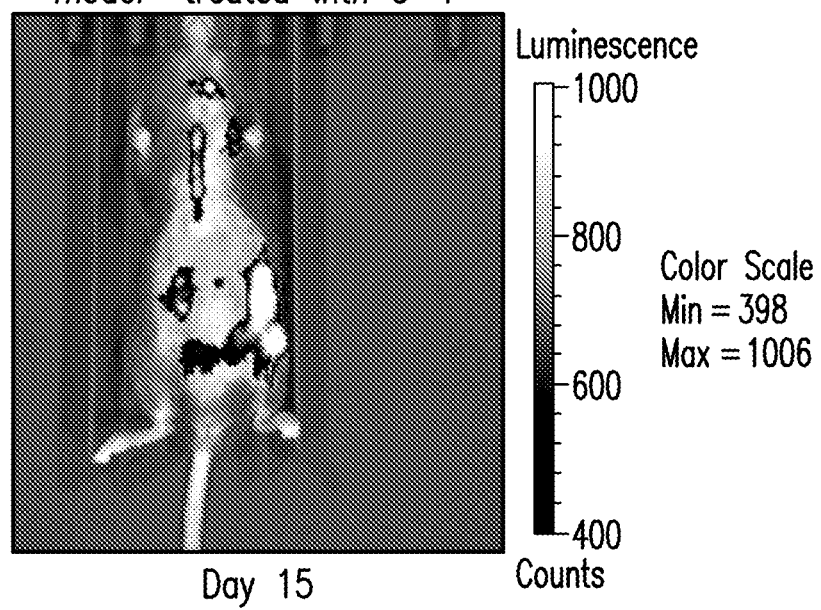

FIG. 11A-C. Thermal shift studies of the interaction between O-4 and p50 or p65.

FIG. 12A-D. Results of an in vivo experiment in which treatment with O-4 resulted in remission of an aggressive lymphoma, as demonstrated in a mouse transgenic for both myc and cherry luciferase reporter genes. (A) day 0 (B) day 4 (C) day 15 (D) NF-κB induced luciferase activity over time; downward arrows indicate treatment with compound O-4 at a dose of 10 mg/kg.

Figure 13:
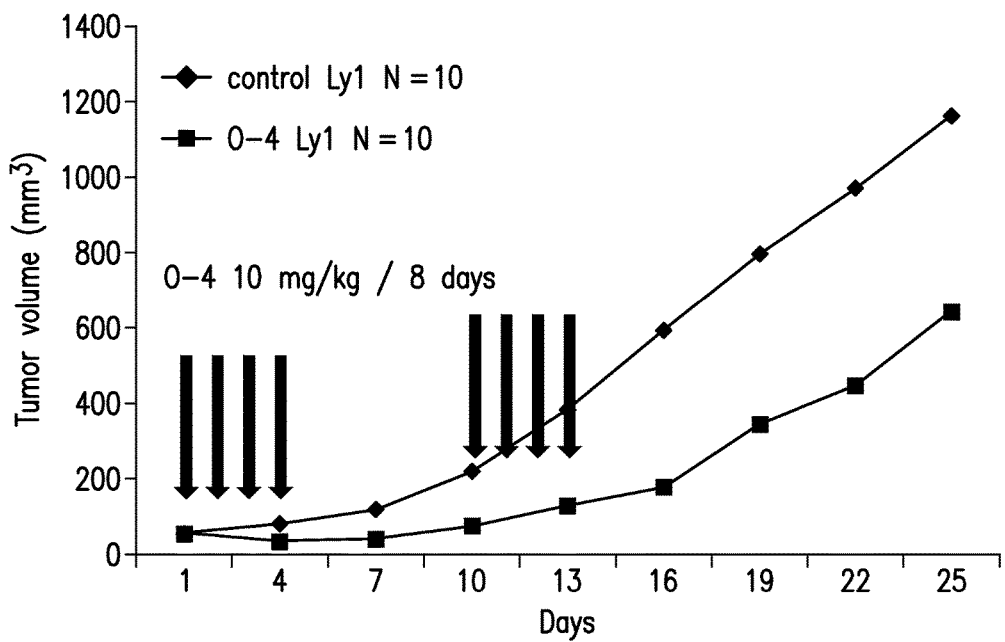

FIG. 13. Results of an in vivo experiment in SCID beige mice with human DLBCL xenografts (OCI-Ly1 cell line) treated with O-4, which significantly inhibited growth of tumors when compared to the control mice which were treated with saline and 10% DMSO; downward arrows indicate treatment with compound O-4 at a dose of 10 mg/kg.

FIG. 14. Compound 47, 55, 69, 74 and 75.

5. DETAILED DESCRIPTION OF THE INVENTION

For clarity of description, and not by way of limitation, the detailed description of the invention is divided into the following subsections:

(i) NQBS and related compounds;
(ii) synthetic schemes for NQBS and related compounds of the invention;
(iii) methods of treatment using NQBS and related compounds; and
(iv) pharmaceutical compositions.

5.1 NQBS and Related Compounds

In particular non-limiting embodiments, the present invention relates to a compound of Formula I:

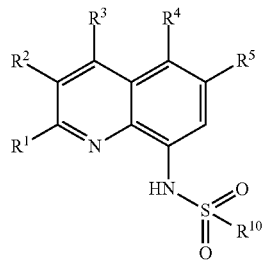

and to salts, esters and prodrugs of the compounds of Formula I. Additionally, the present invention describes methods of synthesizing and using compounds of Formula I. In Formula I:

$R^1$, $R^2$, $R^3$, $R^4$ and $R^5$ are independently selected for each occurrence from the group consisting of hydrogen, halogen, alkyl, cycloalkyl, heterocycloalkyl, aryl, heteroaryl, alkoxy, aryloxy, alkylthiol, arylthiol, CN, and $NO_2$; and $R^{10}$ is selected from the group consisting of substituted or unsubstituted alkyl, substituted or unsubstituted cycloalkyl, substituted or unsubstituted aryl, substituted or unsubstituted heteroaryl and substituted or unsubstituted alkenyl.

In non-limiting embodiments, $R^1$, $R^2$, $R^3$, $R^4$ and $R^5$ are independently selected for each occurrence from the group consisting of hydrogen, branched or unbranched alkyl (e.g., $C_1$-$C_4$ alkyl, for example methyl), alkoxy (e.g., $C_1$-$C_4$ alkoxy, for example methoxy), halogen (e.g. Cl, F, or Br), alkyl halide (e.g. $CF_3$), aryl, CN, alkoxy, aryloxy, $NO_2$, alkylthio, and arylthio. In specific non-limiting embodiments, $R^4$ and $R^5$ are hydrogen, and $R^1$, $R^2$, and $R^3$ are independently hydrogen, halogen, alkyl (e.g., $C_1$-$C_4$ alkyl), aryl, CN, alkoxy, aryloxy, $NO_2$, alkylthio, and arylthio.

In other particular embodiments, $R^{10}$ is selected from the group consisting of substituted or unsubstituted phenyl, substituted or unsubstituted naphthyl, substituted or unsubstituted thiophenyl, substituted or unsubstituted furanyl, substituted or unsubstituted quinolinyl, substituted or unsubstituted isoquinolinyi, 2-Nitrophenyl, 3-Nitrophenyl, 4-Nitrophenyl, 4-Chlorophenyl, 3-fluorophenyl, 4-fluorophenyl, 4-Methyl-2-nitrophenyl, 2-Methyl-5-nitrophenyl, 2-Nitro-4-(trifluoromethyl)phenyl, 4-Methoxy-2-nitrophenyl, 2-Methyl-5-nitrophenyl, 4-Methyl-2-nitrophenyl, 4-Methylphenyl, 2-Aminophenyl, 2-Amino-4-methyl phenyl, Thiophen-2-yl, 5-Chlorothiophen-2-yl, 5,4-dichlorothiophen-2-yl, 5-Bromothiophen-2-yl, 5-chloro-4-bromothiophen-2-yl.

In one subset of non-limiting embodiments, $R^{10}$ of Formula I is a substituted or unsubstituted phenyl, where, if substituted, one or more of the following substituents are present: $C_1$-$C_4$ alkyl, $C_1$-$C_4$ alkoxy, halogen, for example chlorine, fluorine or bromine, halogen-substituted $C_1$-$C_4$ alkyl, amino, or $NO_2$, In specific non-limiting embodiments of this subset, at least three of $R^1$-$R^5$ are H and the remaining R group(s) is $C_1$-$C_4$ alkyl In one subset of non-limiting embodiments, $R^{10}$ of Formula I is a substituted or unsubstituted thiophenyl, where, if substituted, one or more of the following substituents are present: halogen, for example chlorine or bromine, $C_1$-$C_4$ alkyl, or $NO_2$. In specific non-limiting embodiments of this subset, at least three of $R^1$-$R^5$ are H and the remaining R group(s) is $C_1$-$C_4$ alkyl.

In one subset of non-limiting embodiments, $R^{10}$ of Formula I is a substituted or unsubstituted furan, where, if substituted, one or more of the following substituents are present: halogen, for example chlorine or bromine, $C_1$-$C_4$ alkyl, or $NO_2$. In specific non-limiting embodiments of this subset, at least three of $R^1$-$R^5$ are H and the remaining R group(s) is $C_1$-$C_4$ alkyl In other non-limiting embodiments, the present invention relates to a compound of Formula Ia:

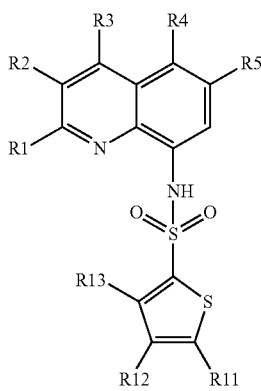

where $R^1$, $R^2$, $R^3$, $R^4$ and $R^5$ are independently selected for each occurrence from the group consisting of hydrogen, branched or unbranched alkyl (e.g., $C_1$-$C_4$ alkyl, for example methyl), alkoxy (e.g., $C_1$-$C_4$ alkoxy, for example methoxy), halogen (e.g. Cl, F, or Br), alkyl halide (e.g. $CF_3$), aryl, CN, alkoxy, aryloxy, $NO_2$, alkylthio, and arylthio. In specific non-limiting embodiments, $R^4$ and $R^5$ are hydrogen, and $R^1$, $R^2$, and $R^3$ are independently hydrogen, halogen, alkyl (e.g., $C_1$-$C_4$ alkyl), aryl, CN, alkoxy, aryloxy, $NO_2$, alkylthio, and arylthio; and where $R^{11}$, $R^{12}$ and $R^{13}$ are independently selected for each occurrence from the group consisting of hydrogen, branched or unbranched alkyl (e.g., $C_1$-$C_4$ alkyl, for example methyl), alkoxy (e.g., $C_1$-$C_4$ alkoxy, for example methoxy), chlorine, bromine, fluorine, $NH_2$ and $NO_2$.

In other non-limiting embodiments, the present invention relates to a compound of Formula II:

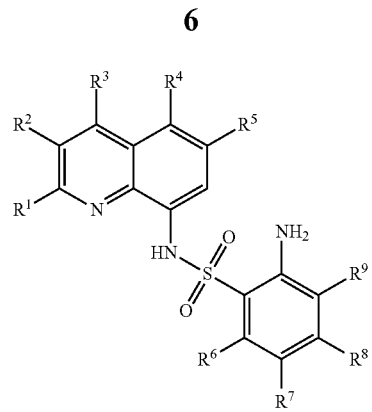

and to salts, esters and prodrugs of the compounds of Formula II. Additionally, the present invention describes methods of synthesizing and using compounds of Formula II. In Formula II:

$R^1$, $R^2$, $R^3$, $R^4$ and $R^5$ are independently selected for each occurrence from the group consisting of hydrogen, halogen, alkyl, cycloalkyl, heterocycloalkyl, aryl, heteroaryl, alkoxy, aryloxy, alkylthiol, arylthiol, CN, and $NO_2$, and in non-limiting embodiments, $R^1$, $R^2$, $R^3$, $R^4$ and $R^5$ are independently selected for each occurrence from the group consisting of hydrogen, branched or unbranched alkyl (e.g., $C_1$-$C_4$ alkyl, for example methyl), alkoxy (e.g., $C_1$-$C_4$ alkoxy, for example methoxy), halogen (e.g. Cl, F, or Br), alkyl halide (e.g. $CF_3$), aryl, CN, alkoxy, aryloxy, $NO_2$, alkylthio, and arylthio. In specific non-limiting embodiments, $R^4$ and $R^5$ are hydrogen, and $R^1$, $R^2$, and $R^3$ are independently hydrogen, halogen, alkyl (e.g., $C_1$-$C_4$ alkyl), aryl, CN, alkoxy, aryloxy, $NO_2$, alkylthio, and arylthio.

$R^6$, $R^7$, $R^8$ and $R^9$ are independently selected for each occurrence from the group consisting of hydrogen, halogen, substituted or unsubstituted alkyl, substituted or unsubstituted cycloalkyl, substituted or unsubstituted aryl, substituted or unsubstituted heteroaryl, substituted or unsubstituted alkoxy, substituted or unsubstituted aryloxy, substituted or unsubstituted alkylthiol, substituted or unsubstituted arylthiol, CN, $NH_2$ and $NO_2$. In a specific non-limiting embodiment, $R^4$ and $R^5$ are hydrogen, and $R^1$, $R^2$, and $R^3$ are independently hydrogen, halogen, alkyl, aryl, CN, alkoxy, aryloxy, $NO_2$, alkylthio, and arylthio.

In a non-limiting embodiment, $R^1$, $R^2$, $R^3$, $R^4$, $R^5$, $R^6$, $R^7$, $R^8$ and $R^9$ are independently selected for each occurrence from the group consisting of hydrogen, methyl, Cl, $OCH_3$, $CF_3$ and F.

In further non-limiting embodiments, the present invention relates to a compound of Formula III:

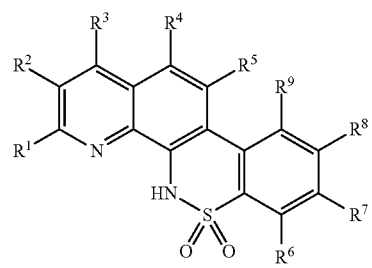

and to salts, esters and prodrugs of the compounds of Formula III. Additionally, the present invention describes methods of synthesizing and using compounds of Formula III. In Formula III:

$R^1$, $R^2$, $R^3$, $R^4$ and $R^5$ are independently selected for each occurrence from the group consisting of hydrogen, halogen, alkyl, cycloalkyl, heterocycloalkyl, aryl, heteroaryl, alkoxy, aryloxy, alkylthiol, arylthiol, CN, and $NO_2$, and in non-limiting embodiments, $R^1$, $R^2$, $R^3$, $R^4$ and $R^5$ are independently selected for each occurrence from the group consisting of hydrogen, branched or unbranched alkyl (e.g., $C_1$-$C_4$ alkyl, for example methyl), alkoxy (e.g., $C_1$-$C_4$ alkoxy, for example methoxy), halogen (e.g. Cl, F, or Br), alkyl halide (e.g. $CF_3$), aryl, CN, alkoxy, aryloxy, $NO_2$, alkylthio, and arylthio. In specific non-limiting embodiments, $R^4$ and $R^5$ are hydrogen, and $R^1$, $R^2$, and $R^3$ are independently hydrogen, halogen, alkyl (e.g., $C_1$-$C_4$ alkyl), aryl, CN, alkoxy, aryloxy, $NO_2$, alkylthio, and arylthio.

$R^6$, $R^7$, $R^8$ and $R^9$ are independently selected for each occurrence from the group consisting of hydrogen, halogen, substituted or unsubstituted alkyl, substituted or unsubsituted cycloalkyl, substituted or unsubstituted aryl, substituted or unsubstituted heteroaryl, substituted or unsubstituted alkoxy, substituted or unsubstituted aryloxy, substituted or unsubstituted alkylthiol, substituted or unsubstituted arylthiol, CN, $NH_2$ and $NO_2$. In a specific non-limiting embodiment, $R^4$ and $R^5$ are hydrogen, and $R^1$, $R^2$, and $R^3$ are independently hydrogen, halogen, alkyl, aryl, CN, alkoxy, aryloxy, $NO_2$, alkylthio, and arylthio.

In a non-limiting embodiment, $R^1$, $R^2$, $R^3$, $R^4$, $R^5$, $R^6$, $R^7$, $R^8$ and $R^9$ are independently selected for each occurrence from the group consisting of hydrogen, methyl, Cl, $OCH_3$, $CF_3$ and F.

The present invention further contemplates the use of compounds that are structurally related to, but fall outside of, the abovelisted formulas. Examples of such related compounds include compounds of Formulas IV and V, as described below.

In certain non-limiting embodiments, the present invention relates to a compound of Formula IV:

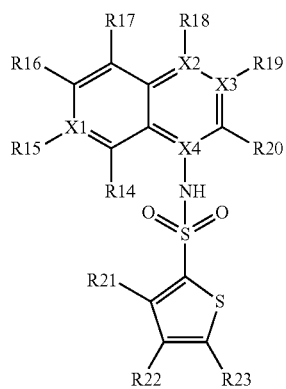

and to salts, esters and prodrugs of the compounds of Formula IV, where $X_1$, $X_2$, $X_3$, and $X_4$ may independently be C or N, where $R^{14}$, $R^{15}$, $R^{16}$, $R^{17}$, $R^{18}$, $R^{19}$, and $R^{20}$ are independently selected for each occurrence from the group consisting of hydrogen, branched or unbranched alkyl (e.g., $C_1$-$C_4$ alkyl, for example methyl), alkoxy (e.g., $C_1$-$C_4$ alkoxy, for example methoxy), halogen (e.g. Cl, F, or Br), and alkyl halide (e.g. $CF_3$), and where $R^{21}$, $R^{22}$, and $R^{23}$ are independently selected for each occurrence from the group consisting of hydrogen, branched or unbranched alkyl (e.g., $C_1$-$C_4$ alkyl, for example methyl), chlorine, bromine, fluorine, $NH_2$ and $NO_2$.

In certain non-limiting embodiments, the present invention relates to a compound of Formula V:

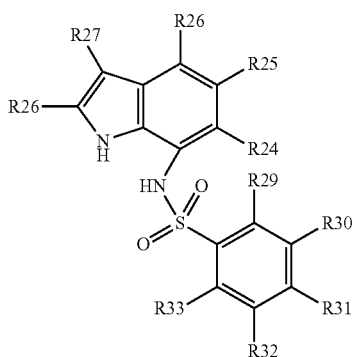

and to salts, esters and prodrugs of the compounds of Formula V, where $R^{24}$, $R^{25}$, $R^{25}$, $R^{27}$, and $R^{28}$ are independently selected for each occurrence from the group consisting of hydrogen, branched or unbranched alkyl (e.g., $C_1$-$C_4$ alkyl, for example methyl), alkoxy (e.g., $C_1$-$C_4$ alkoxy, for example methoxy), halogen (e.g. Cl, F, or Br), or alkyl halide (e.g. $CF_3$), $R^{24}$, $R^{25}$, $R^{26}$, $R^{27}$, and $R^{28}$ are independently selected for each occurrence from the group consisting of hydrogen, branched or unbranched alkyl (e.g., $C_1$-$C_4$ alkyl, for example methyl), alkoxy (e.g., $C_1$-$C_4$ alkoxy, for example methoxy), halogen (e.g. Cl, F, or Br), and alkyl halide (e.g. $CF_3$), and where $R^{29}$, $R^{30}$, $R^{31}$, $R^{32}$, and $R^{33}$ are independently selected for each occurrence from the group consisting of hydrogen, branched or unbranched alkyl (e.g., $C_1$-$C_4$ alkyl, for example methyl), alkoxy (e.g., $C_1$-$C_4$ alkoxy, for example methoxy), halogen (e.g. Cl, F, or Br), alkyl halide (e.g. $CF_3$), $NH_2$ and $NO_2$.

In specific, non-limiting embodiments, compounds that may be used according to the invention include compounds O-1, O-2, O-3, O-4, and O-5 (FIG. 1A-E) and compounds 1-90 (FIG. 8A-W; compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and 90).

In particular non-limiting embodiments, the compound is selected from the group consisting of compounds 19, 47, 55, 69, 74 and 75.

5.2 Synthetic Schemes for NQBS and Related Compounds

In one non-limiting embodiment, compounds of Formula I may be synthesized according to the following scheme:

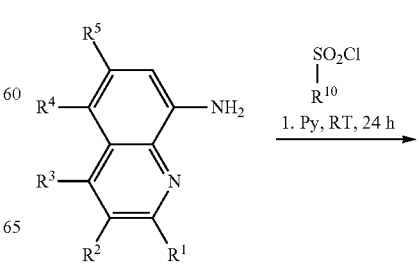

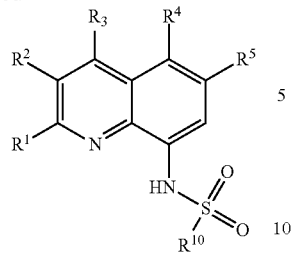

wherein $R^1$, $R^2$, $R^3$, $R^4$, $R^5$ and $R^{10}$ are defined as above for Formula I.

In another non-limiting embodiment, compounds of Formula II may be synthesized according to the following scheme:

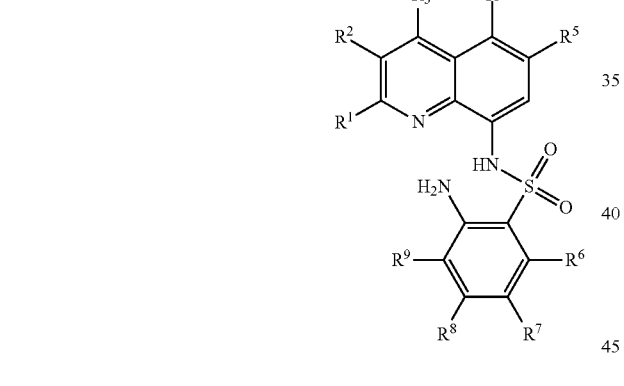

wherein $R^1$, $R^2$, $R^3$, $R^4$, $R^5$, $R^6$, $R^7$, $R^8$ and $R^9$ are defined as above for Formula II.

In other non-limiting embodiments, compounds of Formula II may be synthesized by any means known in the art.

In other non-limiting embodiments, the compounds of Formula II may be synthesized according to the following scheme:

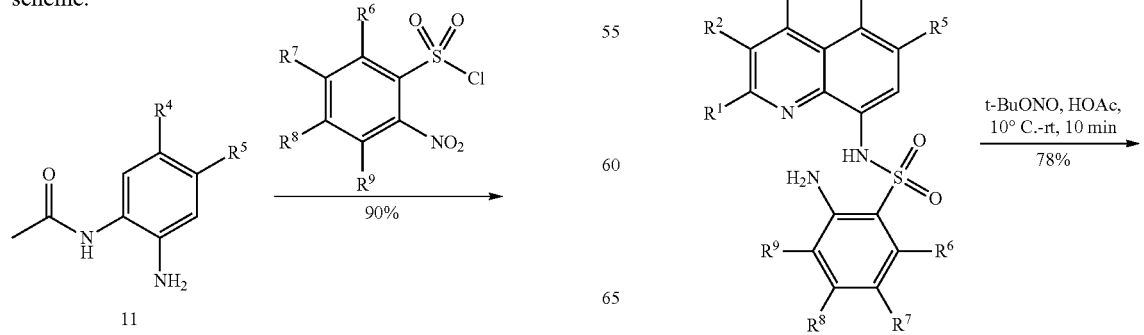

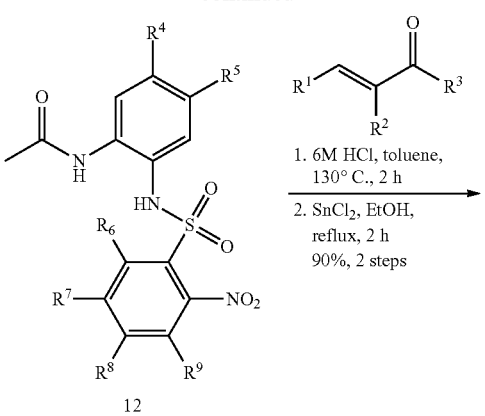

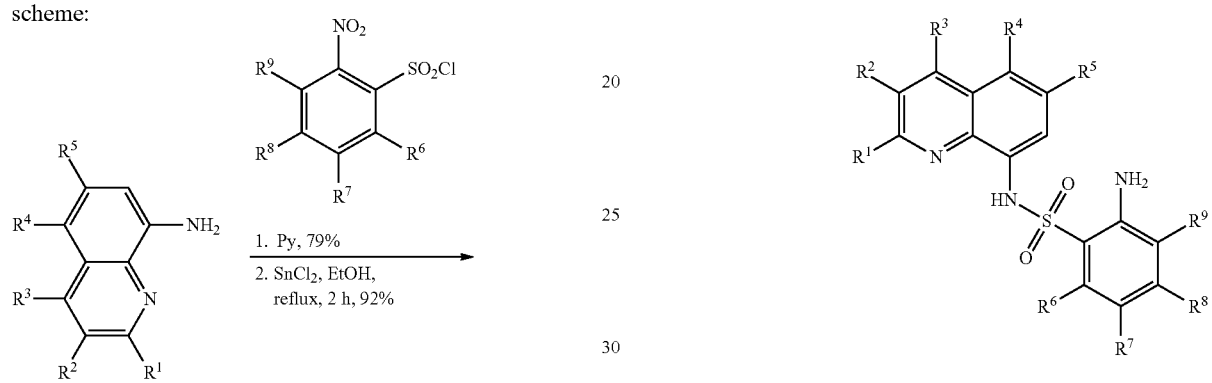

wherein $R^1$, $R^2$, $R^3$, $R^4$, $R^5$, $R^6$, $R^7$, $R^8$ and $R^9$ are defined as above for Formula II.

In non-limiting embodiments, compounds of Formula III may be synthesized according to the following scheme:

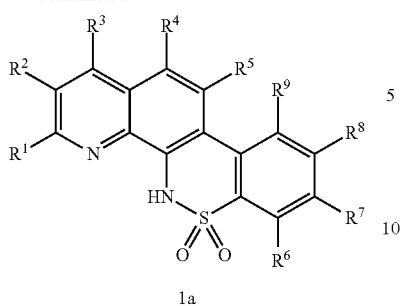

Ia wherein $R^1$, $R^2$, $R^3$, $R^4$, $R^5$, $R^6$, $R^7$, $R^8$ and $R^9$ are defined as above for Formula III.

In other non-limiting embodiments, compounds of Formula III may be synthesized by any means known in the art.

In other non-limiting embodiments, the compounds of Formula III may be synthesized according to the following scheme:

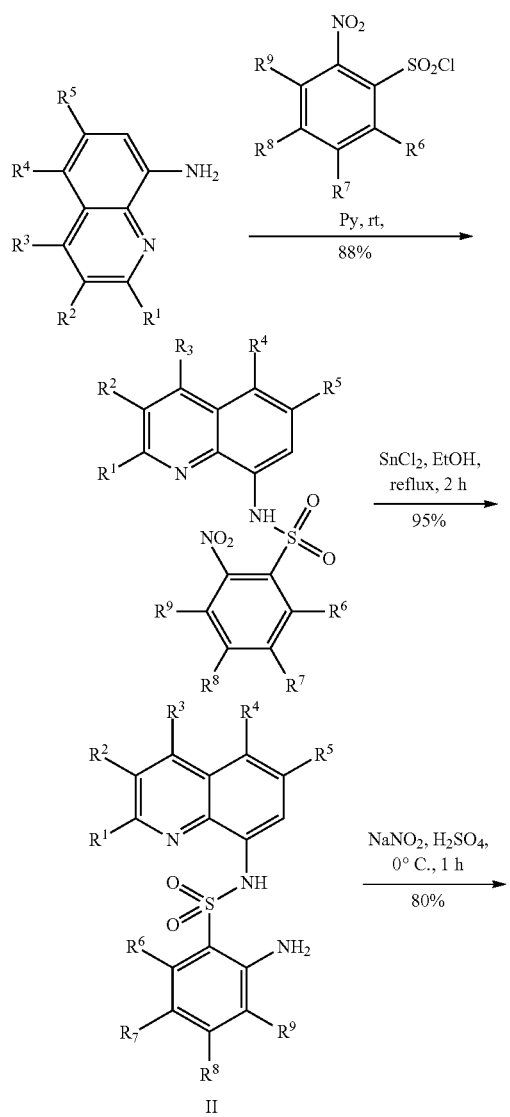

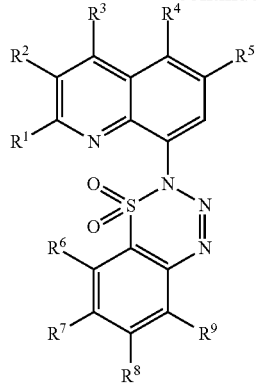

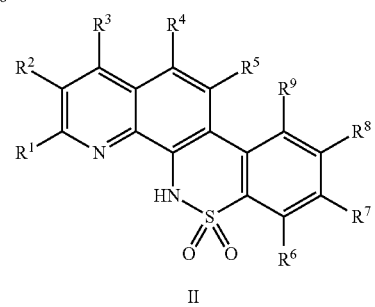

II wherein $R^1$, $R^2$, $R^3$, $R^4$, $R^5$, $R^6$, $R^7$, $R^8$ and $R^9$ are defined as above for Formula III.

Methods analogous to those set forth above may be used to synthesize compounds of formulas Ia, IV and V.

5.3 Methods of Treatment Using NQBS and Related Compounds

In accordance with the invention, there are provided methods of using the compounds of Formulas I-V and compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and 90. The compounds of the instant disclosure can inhibit NFκB activity to exert beneficial effects. A compound of Formula I, Ia, II, III, IV or V or any one or more of compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90, and in particular one or more of compounds 19, 47, 55, 69, 74 and/or 75, that inhibits NFκB activity may be used, in an effective amount, for the treatment of conditions including, but not limited to, cancer (for example, but not limited to, leukemia, lymphoma, glioblastoma, melanoma, squamous cell carcinoma, breast cancer, lung cancer, gastric cancer, liver cancer, renal cancer, pancreatic cancer, colon cancer, ovarian cancer, uterine cancer, cervical cancer, bladder cancer, prostate cancer, and testicular cancer), and inflammatory conditions including, but not limited to, type I hypersensitivity, atopy, anaphylaxis, asthma, osteoarthritis, rheumatoid arthritis, septic arthritis, gout, juvenile idiopathic arthritis, Still's disease, ankylosing spondylitis, inflammatory bowel disease (Ulcerative colitis and Crohn's disease) or inflammation associated with vertebral disc herniation. In addition, the present invention is directed to the treatment of diseases related to dysfunction of cell proliferation, the immune system and/or inflammation.

5.3.1 Treatment of Disease Related to Dysfunction of Cell Proliferation, the Immune System and/or Inflammation In non-limiting embodiments, the present invention provides for methods of treating diseases related to dysfunction of cell proliferation, the immune system and/or inflammation in a subject in need of such treatment by administration of a therapeutic formulation which comprises at least one compound of Formulas I, Ia, II, III, Iv or V, or any one or more of compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 and in particular one or more of compounds 19, 47, 55, 69, 74 and/or 75.

In particular embodiments, the formulation may be administered to a subject in need of such treatment in an amount effective to inhibit NFkB activity. Where the formulation is to be administered to a subject in vivo, the formulation may be administered systemically (e.g., by intravenous injection, oral administration, inhalation, subcutaneous, intramuscular, etc.), intraventricularly, intrathecally, or by any other means known in the art. The amount of the formulation to be administered may be determined using methods known in the art, for example, by performing dose response studies in one or more model system, followed by approved clinical testing in humans.

In one embodiment, the subject or patient has been diagnosed with, or has been identified as having an increased risk of developing a disease associated with dysfunction of cell proliferation, the immune system and/or inflammation.

In other non-limiting embodiments, the present invention provides for methods of reducing in a subject, the risk of inflammatory damage comprising administering to the subject, an effective amount of a composition according to the invention. An effective amount may be a local concentration or, in a pharmaceutical composition, an amount that, when administered to a subject, results in a therapeutic benefit.

According to the invention, an effective amount is an amount of at least one compound of Formulas I, Ia, II, III, IV or V, or any one or more of compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90, and in particular one or more of compounds 19, 47, 55, 69, 74 and/or 75, which reduces one or more clinical symptom of one or more of the aforementioned diseases. Working examples exemplifying experiments for assessing the efficacy of compounds of the invention are set forth below in section 6. For example, the ability of a compound to inhibit proliferation of a cell manifesting a dysfunction in cell proliferation may be used as an indication of effectiveness in vivo. As another example, the ability of a compound to reduce translocation of NF-κB into the nucleus may be used as an indicator.

In a non-limiting embodiment, the effective amount of at least one compound of Formulas I, Ia, II, III, IV or V, or any one or more of compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90, and in particular one or more of compounds 19, 47, 55, 69, 74 and/or 75, may be determined, for example, via an in vitro assay wherein the effective amount of a compound of Formulas I, Ia, II, III, IV or V, or any one or more of compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90, may be correlated with the compound's ability to reduce the nuclear translocation of NFκB. By way of example, and not of limitation, such an assay may comprise a cell-based assay that utilizes an agent, for example, a cytokine such as TNFα, to stimulate nuclear translocation of endogenous NFkB. Stimulation by the agent may result in proteasome degradation of IkBα and subsequent translocation of NFkB from the cytoplasm to the nucleus, while in the absence of such a stimulatory agent, NFkB is sequestered in the cytoplasm due to its binding to IkBα.

In the nuclear-translocation in vitro assay, nuclear translocation of NFkB, for example, the endogenous p65 RelA subunit, may be detected and/or measured following stimulation with the agent through the use of, for example, but not limited to, fluorescent antibody detection and an automated imaging platform. Compounds of the invention may be contacted with cells of the in vitro assay, wherein a reduction in NFkB nuclear transport compared to a cell not contacted with the compound is indicative of the compound's ability to inhibit NFkB activity. According to the invention, a reduction in nuclear translocation of NFκB may be correlative with the compound's therapeutic efficacy.

In one embodiment, an effective amount of a compound of Formulas I, Ia, II, III, IV or V, or any one or more of compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90, and in particular one or more of compounds 19, 47, 55, 69, 74 and/or 75, may be correlated with the compound's ability to inhibit NFκB induced gene activation, wherein a greater level of inhibition at a lower concentration when compared to a control level of inhibition, for example, as exhibited by a known NFκB nuclear-translocation inhibitor, such as BAY 11-7082, is indicative of greater therapeutic efficacy of the compound.

In one embodiment, an effective amount of a compound of Formulas I, Ia, II, III, IV, or V, or any one or more of compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90, and in particular one or more of compounds 19, 47, 55, 69, 74 and/or 75, may be that amount which inhibits NFκB induced gene activation with an efficacy of at least about 10-20%, at least about 20-50%, at least about 50-80%, or at least about 80-100% or more when compared to the NFκB induced gene activation inhibition achieved by a known inhibitor, such as BAY 11-7082.

In one non-limiting embodiment, an effective amount of a compound of Formulas Ia, II, III, IV, or V, or any one or more of compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90, and in particular one or more of compounds 19, 47, 55, 69, 74 and/or 75, may be that amount which inhibits NFκB nuclear-translocation by at least 50% when the compound is administered at a concentration ranging from about 200 μM to about 0.01 μM, preferably from about 100 μM to about 0.01 μM, more preferably from about 50 μM to about 0.01 μM, and more preferably from about 10 μM to about 0.01 μM in the in vitro assay, wherein inhibition of NFκB nuclear-translocation at a lower concentration in the in vitro assay is correlative with the compound's therapeutic efficacy.

In another non-limiting embodiment, the effective amount of at least one compound of Formulas I, Ia, II, III, IV, or V, or any one or more of compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90, and in particular one or more of compounds 19, 47, 55, 69, 74 and/or 75, may be determined, for example, via an in vitro assay wherein the effective amount of a compound of Formulas I, Ia, II, III, IV, or V, or any one or more of compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90, may be correlated with the compound's ability to reduce expression of an NFκB-dependent reporter construct, for example, a β-lactamase reporter (NFκB-bla). By way of example, and not of limitation, such an assay may comprise contacting a cell expressing the NFκB-dependent reporter construct, and monitoring the level of β-lactamase expression, wherein a decrease in expression compared to a cell not contacted with the compound indicates a reduction in NFκB activity. According to the invention, the reduction in expression of the NFκB-dependent reporter may be correlative with the compound's therapeutic efficacy.

In one non-limiting embodiment, an effective amount of a compound of Formulas I, II, III, IV or V, or any one or more of compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90, and in particular one or more of compounds 19, 47, 55, 69, 74 and/or 75, may be that amount which reduces expression of an NFκB-bla construct by at least 50% when the compound is administered at a concentration ranging from about 200 μM to about 0.01 μM, preferably from about 100 μM to about 0.01 μM, more preferably from about 50 μM to about 0.01 μM, and more preferably from about 10 μM to about 0.01 μM in the in vitro assay, wherein a reduction of NFκB-bla expression at a lower concentration in the in vitro assay is correlative with the compound's therapeutic efficacy.

In one non-limiting embodiment, an effective amount of a compound of Formulas I, II, III, IV, or V, or any one or more of compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90, and in particular one or more of compounds 19, 47, 55, 69, 74 and/or 75, may be an amount which achieves a local concentration at the therapeutic site of about 100 μM to about 0.01 μM, preferably from about 50 μM to about 0.01 μM, more preferably from about 20 μM to about 0.01 μM, and more preferably from about 10 μM to about 0.01 μM in the in vitro assay.

5.3.2 Administration of Treatments

According to the invention, the component or components of a pharmaceutical composition of the invention may be administered to a subject by means including but not limited to intravenous, intra-arterial, intramuscular, intradermal, transdermal, subcutaneous, oral, intraperitoneal, intraventricular, and/or intrathecal administration.

In particular non-limiting embodiments, the therapeutic compound can be delivered in a controlled or sustained release system. For example, a compound or composition may be administered using intravenous infusion, an implantable osmotic pump, a transdermal patch, liposomes, or other modes of administration. In one embodiment, a pump may be used (see Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Langer and Wise eds., 1974, Medical Applications of Controlled Release, CRC Press: Boca Raton, Fla.; Smolen and Ball eds., 1984, Controlled Drug Bioavailability, Drug Product Design and Performance, Wiley, N.Y.; Ranger and Peppas, 1983, J. Macromol. Sci. Rev. Macromol. Chem., 23:61; Levy et al., 1985, Science 228:190; During et al., 1989, Ann. Neural., 25:351; Howard et al., 9189, J. Neurosurg. 71:105). In yet another embodiment, a controlled release system can be placed in proximity of the therapeutic target, i.e., the heart or a blood vessel, thus requiring only a fraction of the systemic dose (see, e.g., Goodson, 1984, in Medical Applications of Controlled Release, supra, Vol. 2, pp. 115-138). Other controlled release systems known in the art may also be used.

5.4 Pharmaceutical Compositions

The compounds and compositions of the invention may be formulated as pharmaceutical compositions by admixture with a pharmaceutically acceptable carrier or excipient.

For example, the pharmaceutical composition may comprise an effective amount of at least one compound of Formulas I, Ia, II, III, IV or V, or any one or more of compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90, and in particular one or more of compounds 19, 47, 55, 69, 74 and/or 75, and a physiologically acceptable diluent or carrier. The pharmaceutical composition may further comprise a second drug, for example, but not by way of limitation, an anti-cancer drug, an anti-inflammatory drug, for example, but not limited to, a steroid compound and/or a non-steroidal anti-inflammatory drug.

The phrase "pharmaceutically acceptable" indicates that a substance is physiologically tolerable when administered to a subject. Preferably, but not by way of limitation, as used herein, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, or, for solid dosage forms, may be standard tabletting excipients. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition, or other editions.

In a specific embodiment, the therapeutic compound can be delivered in a vesicle, in particular a liposome (see Langer, 1990, Science 249; 1527-1533; Treat et al., 1989, in Liposomes in the Therapy of Infectious Disease and Cancer, Lopez-Berestein and Fidler eds., Liss: New York, pp. 353-365; Lopez-Berestein, ibid., pp. 317-327; see generally Lopez-Berestein, ibid.).

The present invention is not to be limited in scope by the specific embodiments described herein and the Examples that follow. Indeed, various modifications of the invention in addition to those described herein will become apparent to those skilled in the art from the foregoing description and the accompanying Examples and Figures. Such modifications are intended to fall within the scope of the appended claims.

6. WORKING EXAMPLE

Using a novel cell based assay, a unique scaffold structure of NQBS compounds has been identified having either the C7 locked or C7 open configuration (FIG. 1) that appears to selectively inhibit NF-κB mediated gene activation. In particular, a series of first, second and third generation compounds have been screened and found to exhibit the following properties.

Figure 3B:
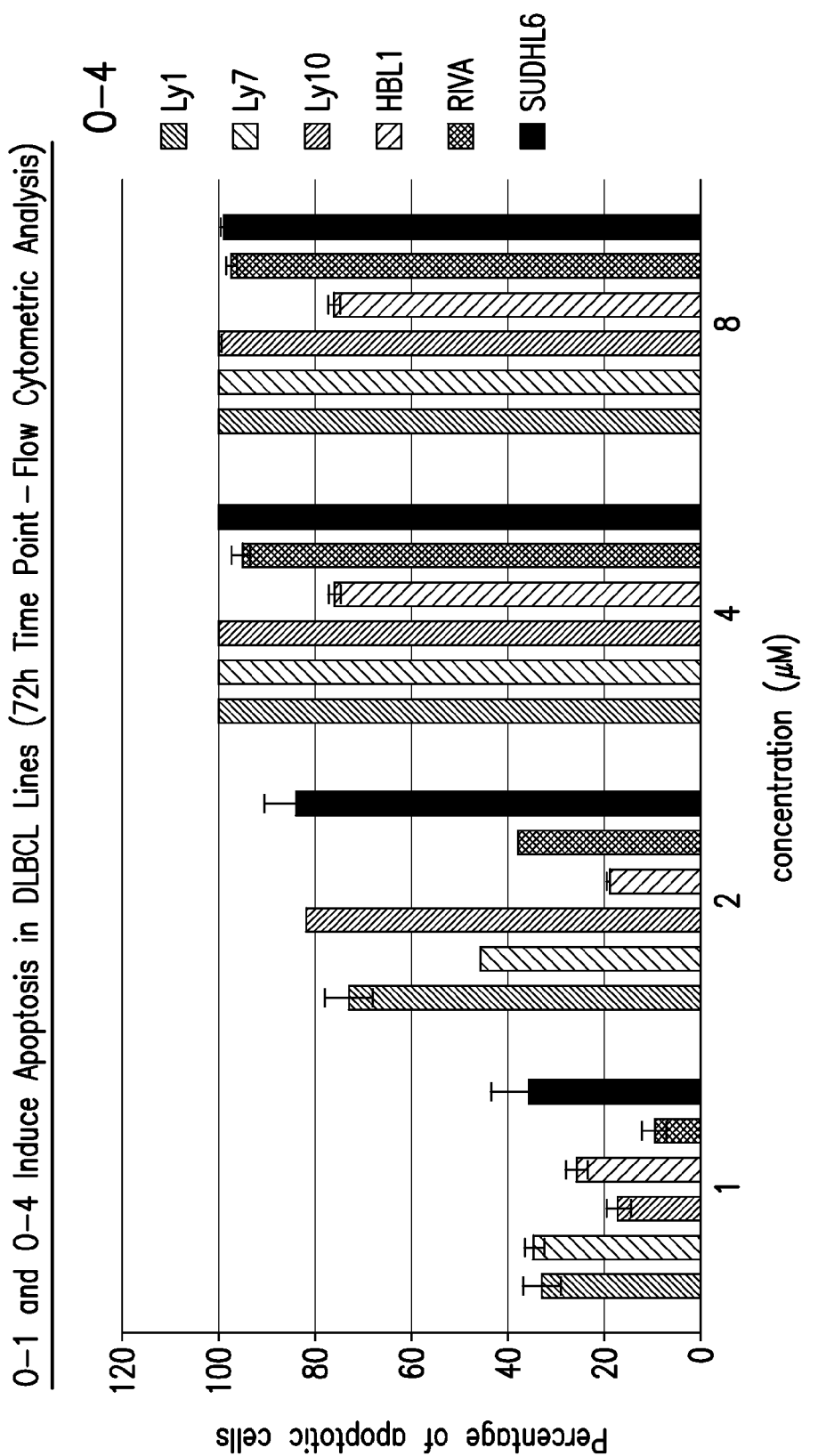

Both C-7 closed and open configurations of compound were found to exhibit potent and reproducible concentration dependent cytotoxicity and induction of apoptosis in a panel of 12 highly drug resistant lymphoma cell lines (including B- and T-cell lymphomas), with low micromolar potency (FIGS. 2 and 3). The O-1 and O-4 (as well as O-2 and O-3) analogs were found to be highly potent in both GC and ABC DLBCL (O-5 was found to be inactive). While C7 open structures appeared to be more potent, there were minimal differences in the activities of these compounds. Cytotoxicity was not found to be significantly influenced by the duration of exposure, FIG. 3 shows the results of flow cytometric analysis of DLBCL cell lines treated with compound O-1 or O-4 for 72 hours. Although both compounds were found to induce apoptosis in these cells, the C7 open structure (O-4) was found to induce more apoptosis across a diverse panel of DLBCL cells relative to the O-1, the closed structure.

Treatment of these cell lines with the NQBS analogs was observed to sequester the p50 subunit to the cytoplasm (FIG. 4A-B), which has been confirmed using a 'gold standard' electrophoretic mobility shift assay ("EMSA"; FIG. 5). The NQBS compounds tested were found not to affect other non-NF-κB dependent transcription factors involved in normal cell cycle regulation (e.g.: MCM3 and Ku80) (FIG. 6). Further, open ring structure NQBS compounds were found not to exhibit significant toxicity in SCID beige mice (no weight loss and no toxic deaths) at doses as high as 10 mg/kg, well in excess of the in vitro IC50 (FIG. 7).

The foregoing analysis was used to generate structure activity relationships (SAR) that have informed new rounds of synthesis, producing additional NQBS structures (FIGS. 8A-J). The results of in vitro cytotoxicitry screens of these compounds demonstrating their activity is shown in FIG. 9.

A binding site has been predicted for NQBS within the RHD of both p65 and p50 (FIG. 10), supporting the hypothesis regarding the potential novel mechanism of action (MOA) for this class of compounds. Direct binding data using thermal shift assays was also obtained, further corroborating the MOA (FIG. 11A-C).

Finally, using a transgenic mouse created to represent an in vivo model for aggressive lymphoma, it has been shown that one of the NQBS analogs (O-4) produces a complete remission of the lymphoma following daily dosing (FIG. 12A-D).

Furthermore, activity of O-4 was shown in SCID beige mice with human DLBCL xenografts, where O-4 significantly inhibited growth of tumors compared to the control (FIG. 13).

Various publications are cited herein, the contents of which are hereby incorporated by reference in their entireties.

What is claimed is:

1. A compound having the formula:

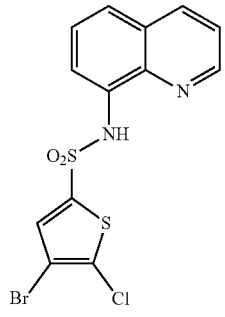

2. A composition comprising in an effective amount a compound having the formula:

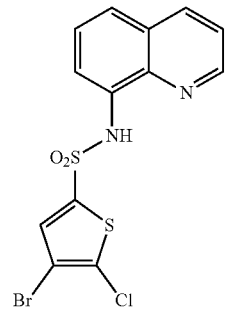

* * * * *

UNITED STATES PATENT AND TRADEMARK OFFICE
CERTIFICATE OF CORRECTION

| | | |
|---|---|---|
| PATENT NO. | : 9,896,420 B2 | Page 1 of 1 |
| APPLICATION NO. | : 14/020363 | |
| DATED | : February 20, 2018 | |
| INVENTOR(S) | : Donald W. Landry et al. | |

It is certified that error appears in the above-identified patent and that said Letters Patent is hereby corrected as shown below:

On the Title Page

At item (72) Inventors:
"Kristen Alison Rinderspacher, Bronx, NY (US)"
Should read:
-- Kirsten Alison Rinderspacher, Bronx, NY (US) --

Signed and Sealed this
Twenty-sixth Day of June, 2018

Andrei Iancu
*Director of the United States Patent and Trademark Office*

SEQUENCE LISTING

```
<160> NUMBER OF SEQ ID NOS: 1

<210> SEQ ID NO 1
<211> LENGTH: 308
<212> TYPE: PRT
<213> ORGANISM: Homo sapiens

<400> SEQUENCE: 1

Leu Ser Gln Leu Thr Thr Asp Asn Lys Gly Asn Ser Lys Ala Gly Asn
1               5                   10                  15

Gly Thr Leu Glu Asn Gln Lys Gly Thr Gly Val Lys Lys Ser Pro Met
            20                  25                  30

Leu Cys Gly Gln Tyr Pro Val Lys Ser Glu Gly Lys Glu Leu Lys Ile
        35                  40                  45
```

```
Val Val Gln Pro Glu Thr Gln His Arg Ala Arg Tyr Leu Thr Glu Gly
    50              55                  60
Ser Arg Gly Ser Val Lys Asp Arg Thr Gln Gln Gly Phe Pro Thr Val
65              70                  75                  80
Lys Leu Glu Gly His Asn Glu Pro Val Val Leu Gln Val Phe Val Gly
                85              90                  95
Asn Asp Ser Gly Arg Val Lys Pro His Gly Phe Tyr Gln Ala Cys Arg
            100             105                 110
Val Thr Gly Arg Asn Thr Thr Pro Cys Lys Glu Val Asp Ile Glu Gly
        115             120                 125
Thr Thr Val Ile Glu Val Gly Leu Asp Pro Ser Asn Asn Met Thr Leu
        130             135                 140
Ala Val Asp Cys Val Gly Ile Leu Lys Leu Arg Asn Ala Asp Val Glu
145             150             155                 160
Ala Arg Ile Gly Ile Ala Gly Ser Lys Lys Ser Thr Arg Ala Arg
            165             170             175
Leu Val Phe Arg Val Asn Ile Met Arg Lys Asp Gly Ser Thr Leu Thr
        180             185                 190
Leu Gln Thr Pro Ser Ser Pro Ile Leu Cys Thr Gln Pro Ala Gly Val
        195             200                 205
Pro Glu Ile Leu Lys Lys Ser Leu His Ser Cys Ser Val Lys Gly Glu
    210             215                 220
Glu Glu Val Phe Leu Ile Gly Lys Asn Phe Leu Lys Gly Thr Lys Val
225             230             235                 240
Ile Phe Gln Glu Asn Val Ser Asp Glu Asn Ser Trp Lys Ser Glu Ala
            245             250                 255
Glu Ile Asp Met Glu Leu Phe His Gln Asn His Leu Ile Val Lys Val
            260             265                 270
Pro Pro Tyr His Asp Gln His Ile Thr Leu Pro Val Ser Val Gly Ile
            275             280                 285
Tyr Val Val Thr Asn Ala Gly Arg Ser His Asp Val Gln Pro Phe Thr
        290             295                 300
Tyr Thr Pro Asp
305
```